(12) United States Patent
Noessner et al.

(10) Patent No.: US 11,365,237 B2
(45) Date of Patent: Jun. 21, 2022

(54) FUSION PROTEINS OF PD-1 AND 4-1BB

(71) Applicant: HELMHOLTZ ZENTRUM MUENCHEN-DEUTSCHES FORSCHUNGSZENTRUM FUER GESUNDHEIT UND UMWELT (GMBH), Neuherberg (DE)

(72) Inventors: Elfriede Noessner, Munich (DE); Ramona Schlenker, Munich (DE); Stephan Weisz, Freising (DE)

(73) Assignee: HELMHOLTZ ZENTRUM MUENCHEN—DEUTSCHES FORSCHUNGSZENTRUM FUER GESUNDHEIT UND UMWELT (GMBH), Neuherberg (DE)

( * ) Notice: Subject to any disclaimer, the term of this patent is extended or adjusted under 35 U.S.C. 154(b) by 311 days.

(21) Appl. No.: 16/087,262

(22) PCT Filed: Mar. 23, 2017

(86) PCT No.: PCT/EP2017/056931
§ 371 (c)(1),
(2) Date: Sep. 21, 2018

(87) PCT Pub. No.: WO2017/162797
PCT Pub. Date: Sep. 28, 2017

(65) Prior Publication Data
US 2019/0106478 A1      Apr. 11, 2019

(30) Foreign Application Priority Data

Mar. 23, 2016 (LU) .......................................... 93006

(51) Int. Cl.
| C07K 14/705 | (2006.01) |
| C12N 15/62 | (2006.01) |
| A61P 35/00 | (2006.01) |

(52) U.S. Cl.
CPC .. *C07K 14/70578* (2013.01); *C07K 14/70503* (2013.01); *C07K 14/70532* (2013.01); *C12N 15/62* (2013.01); *C07K 2319/03* (2013.01); *C07K 2319/74* (2013.01)

(58) Field of Classification Search
None
See application file for complete search history.

(56) References Cited

U.S. PATENT DOCUMENTS

| 2014/0242049 A1* | 8/2014 | Choi ................. C07K 14/70521 424/93.21 |
| 2014/0271635 A1* | 9/2014 | Brogdon .......... C07K 14/70503 424/133.1 |
| 2015/0307623 A1* | 10/2015 | Abbot .................... C07K 16/30 435/328 |
| 2017/0166622 A1* | 6/2017 | Baeuerle ............ C07K 16/2803 |
| 2017/0209492 A1* | 7/2017 | June ................ A61K 39/001113 |
| 2017/0226216 A1* | 8/2017 | Morgan ................... A61P 13/12 |
| 2017/0335281 A1* | 11/2017 | Loew ............. A61K 39/001164 |
| 2017/0360913 A1* | 12/2017 | Zhao .............. A61K 39/001157 |
| 2018/0002435 A1* | 1/2018 | Sasu ................ C07K 14/70535 |
| 2018/0044404 A1* | 2/2018 | Oda ........................ A61P 31/12 |
| 2018/0185434 A1* | 7/2018 | Borrello ........... C07K 14/70521 |
| 2018/0273601 A1* | 9/2018 | Adusumilli .... A61K 39/001157 |
| 2019/0010207 A1* | 1/2019 | Kobold ............ C07K 14/70521 |
| 2019/0175652 A1* | 6/2019 | Abbot ..................... A61P 35/00 |
| 2019/0241910 A1* | 8/2019 | Jarjour .................. C12N 15/907 |
| 2019/0292533 A1* | 9/2019 | Nager ................... C07K 14/715 |
| 2021/0079349 A1* | 3/2021 | Wu ......................... C07K 16/30 |
| 2021/0087251 A1* | 3/2021 | Corey ................... C07K 14/705 |

FOREIGN PATENT DOCUMENTS

| CN | 104114233 A | 10/2014 |
| CN | 104829733 A | 8/2015 |
| CN | 105246912 A | 1/2016 |
| CN | 105377897 A | 3/2016 |
| CN | 105392888 A | 3/2016 |
| WO | 2013019615 A2 | 2/2013 |
| WO | 2015142675 A2 | 9/2015 |
| WO | 2016141357 A1 | 9/2016 |

OTHER PUBLICATIONS

Riley J.L. Immunol Rev. May 2009 ; 229(1): 114-125.*
Liu et al. (2016) Cancer Res 76: 1578-1590.*
NCBI Reference Sequence NP_005009.2 (2021), 3 pages.*
Tang et al., American Journal of Translational Research, Mar. 15, 2015, vol. 7, No. 3, pp. 460-473, E-Century Publishing Corporation.
Ankri et al., The Journal of Immunology, The American Association of Immunologists, Oct. 1, 2013, vol. 191, No. 8, pp. 4121-4129.
Kobold et al., Journal of the National Cancer Institute, Oxford University Press, Jun. 23, 2015, vol. 107, No. 8, pp. djv146-1.
PCT International Search Report and Written Opinion dated May 9, 2017 from corresponding Application No. PCT/EP2017/056931, 15 pages.
Schlenker, R., Chimeric co-stimulatory receptors as a strategy to improve the performance of T cells in tumor environment, Dissertation, 2015, pp. 1-132.

(Continued)

*Primary Examiner* — Ilia I Ouspenski
(74) *Attorney, Agent, or Firm* — Dilworth IP, LLC

(57) ABSTRACT

The present invention relates to fusion proteins comprising (a) an extracellular domain containing a polypeptide derived from PD-1 or CD40L at its N-terminus; (b) a transmembrane domain; and (c) an intracellular domain containing a polypeptide derived from 4-1BB or CD28 at its C-terminus. Also, fusion proteins with CD28 at the N-terminus and CD40L at the C-terminus are envisaged. The present invention also relates to nucleic acid molecules encoding such fusion proteins, vectors containing such nucleic acid molecules, and host cells containing such vectors. The present invention further relates to methods for producing such host cells. Finally, the present invention relates to pharmaceutical compositions comprising such fusion proteins, nucleic acid molecules, vectors, and/or host cells, particularly for treating diseases or disorders associated with PD-1/PD-L2 or CD40 binding and/or PD-L1/PD-L2 or CD40 expression such as cancer and chronic viral infection.

14 Claims, 17 Drawing Sheets

Specification includes a Sequence Listing.

(56) References Cited

OTHER PUBLICATIONS

Office Action issued in JP Patent Application No. 2018-549452 dated Jul. 28, 2020.
Office Action and Search Report issued in Chinese Patent Application No. 201780031958.9 dated Apr. 30, 2021, 13 pages.
"UniprotKB-Q15116 (PDCD1_HUMAN)", Programmed cell death protein 1. Apr. 17, 2007, pp. 1-14.

* cited by examiner

Figure 1

SEQ ID NO: 1

ATGCAGATTCCTCAGGCCCCTTGGCCTGTCGTGTGGGCTGTGCTCCAGCTGGGATGGC
GGCCTGGCTGGTTTCTGGACAGCCCCGACAGACCCTGGAACCCCCCTACATTTTCCCC
TGCCCTGCTGGTCGTGACCGAGGGCGACAATGCCACCTTCACCTGTAGCTTCAGCAAC
ACCAGCGAGAGCTTCGTGCTGAACTGGTACAGAATGAGCCCCAGCAACCAGACCGACA
AGCTGGCCGCCTTCCCCGAGGATAGATCTCAGCCCGGCCAGGATTGCCGGTTCAGAGT
GACCCAGCTGCCCAACGGCCGGGACTTCCACATGTCTGTCGTGCGGGCCAGACGGAA
CGACAGCGGCACATATCTGTGCGGCGCCATCAGCCTGGCCCCAAGGCCCAGATCAAA
GAGAGCCTGAGAGCCGAGCTGAGAGTGACCGAGAGAAGGGCCGAAGTGCCTACCGCC
CACCCTAGCCCATCTCCAAGACCTGCCGGCCAG

SEQ ID NO: 2

MQIPQAPWPVVWAVLQLGWRPGWFLDSPDRPWNPPTFSPALLVVTEGDNATFTCSFSNT
SESFVLNWYRMSPSNQTDKLAAFPEDRSQPGQDCRFRVTQLPNGRDFHMSVVRARRNDS
GTYLCGAISLAPKAQIKESLRAELRVTERRAEVPTAHPSPSRPAGQ

SEQ ID NO: 3

AAGCGGGGCAGAAAGAAGCTGCTGTACATCTTCAAGCAGCCCTTCATGCGGCCCGTGC
AGACCACCCAGGAAGAGGACGGCTGCTCCTGCCGGTTTCCCGAGGAAGAAGAGGGGG
GCTGCGAGCTCTAA

SEQ ID NO: 4

*KRGRKKLLYIFKQPFMRPVQTTQEEDGCSCRFPEEEEGGCEL*

SEQ ID NO: 5

ATTATCTCATTCTTCCTGGCCCTGACCTCTACCGCCCTGCTGTTTCTGCTGTTCTTTCTG
ACCCTGCGGTTCAGCGTCGTG

SEQ ID NO: 6

<u>IISFFLALTSTALLFLLFFLTLRFSVV</u>

SEQ ID NO: 7

TTCCAGACACTGGTCGTGGGAGTCGTGGGCGGCCTGCTGGGATCTCTGGTGCTGCTCG
TGTGGGTGCTGGCCGTGATC

SEQ ID NO: 8

<u>FQTLVVGVVGGLLGSLVLLVWVLAVI</u>

SEQ ID NO: 9 atgcagatcccacaggcgccctggccagtcgtctgggcggtgctacaactgggctggcggccaggatggttcttagactcccca
gacaggccctggaaccccccccaccttctccccagccctgctcgtggtgaccgaaggggacaacgccaccttcacctgcagcttc
tccaacacatcggagagcttcgtgctaaactggtaccgcatgagccccagcaaccagacggacaagctggccgccttccccga
ggaccgcagccagcccggccaggactgccgcttccgtgtcacacaactgcccaacgggcgtgacttccacatgagcgtggtca
gggcccggcgcaatgacagcggcacctacctctgtggggccatctccctggcccccaaggcgcagatcaaagagagcctgcg
ggcagagctcagggtgacagagagaagggcagaagtgcccacagcccaccccagccctcacccaggccagccggccag
ttccaaaccctggtggttggtgtcgtgggcggcctgctgggcagcctggtgctgctagtctgggtcctggccgtcatctgctcccggg
ccgcacgagggacaataggagccaggcgcaccggccagcccctgaaggaggacccctcagccgtgcctgtgttctctgtgga
ctatggggagctggatttccagtggcgagagaagaccccggagcccccgtgccctgtgtccctgagcagacggagtatgcca
ccattgtctttcctagcggaatgggcacctcatccccgcccgcaggggctcagctgacggccctcggagtgcccagccactgg
gcctgaggatggacactgctcttggcccctctga

SEQ ID NO: 10

MQIPQAPWPVVWAVLQLGWRPGWFLDSPDRPWNPPTFSPALLVVTEGDNATFTCSFSNT
SESFVLNWYRMSPSNQTDKLAAFPEDRSQPGQDCRFRVTQLPNGRDFHMSVVRARRNDS
GTYLCGAISLAPKAQIKESLRAELRVTERRAEVPTAHPSPSPRPAGQ<u>FQTLVVGVVGGLLGS
LVLLVWVLAVI</u>CSRAARGTIGARRTGQPLKEDPSAVPVFSVDYGELDFQWREKTPEPPVPC
VPEQTEYATIVFPSGMGTSSPARRGSADGPRSAQPLRPEDGHCSWPL

SEQ ID NO: 11 atgggaaacagctgttacaacatagtagccactctgttgctggtcctcaactttgagaggacaagatcattgcaggatccttgtagt
aactgcccagctggtacattctgtgataataacaggaatcagatttgcagtccctgtcctccaaatagtttctccagcgcaggtgga
caaaggacctgtgacatatgcaggcagtgtaaaggtgttttcaggaccaggaaggagtgttcctccaccagcaatgcagagtgt
gactgcactccaggtttcactgcctgggggcaggatgcagcatgtgtgaacaggattgtaaacaaggtcaagaactgacaaa
aaaaggttgtaaagactgttgctttgggacatttaacgatcagaaacgtggcatctgtcgaccctggacaaactgttctttggatgga
aagtctgtgcttgtgaatgggacgaaggagagggacgtggtctgtggaccatctccagccgacctctctccgggagcatcctctgt
gaccccgcctgccctgcgagagagccaggacactctccgcagatcatctccttctttcttgcgctgacgtcgactgcgttgctcttc
ctgctgttcttcctcacgctccgtttctctgttgttaaacggggcagaaagaaactcctgtatatattcaaacaaccatttatgagacca
gtacaaactactcaagaggaagatggctgtagctgccgatttccagaagaagaagaaggaggatgtgaactgtga

SEQ ID NO: 12

MGNSCYNIVATLLLVLNFERTRSLQDPCSNCPAGTFCDNNRNQICSPCPPNSFSSAGGQR
TCDICRQCKGVFRTRKECSSTSNAECDCTPGFHCLGAGCSMCEQDCKQGQELTKKGCKD

CONT. Figure 1

CCFGTFNDQKRGICRPWTNCSLDGKSVLVNGTKERDVVCGPSPADLSPGASSVTPPAPAR
EPGHSPQ<u>IISFFLALTSTALLFLLFFLTLRFSVV</u>***KRGRKKLLYIFKQPFMRPVQTTQEEDGCS
CRFPEEEEGGCEL***

SEQ ID NO: 13
atgctcaggctgctcttggctctcaacttattcccttcaattcaagtaacaggaaacaagattttggtgaagcagtcgcccatgcttgt
agcgtacgacaatgcggtcaaccttagctgcaagtattcctacaatctcttctcaagggagttccgggcatcccttcacaaaggact
ggatagtgctgtggaagtctgtgttgtatatgggaattactcccagcagcttcaggtttactcaaaaacggggttcaactgtgatggg
aaattgggcaatgaatcagtgacattctacctccagaatttgtatgttaaccaaacagatatttacttctgcaaaattgaagttatgtat
cctcctccttacctagacaatgagaagagcaatggaaccattatccatgtgaaagggaaacacctttgtccaagtcccctatttccc
ggaccttctaagcccttttgggtgctggtggtggttggtggagtcctggcttgctatagcttgctagtaacagtggcctttattattttctgg
gtgaggagtaagaggagcaggctcctgcacagtgactacatgaacatgactccccgccgcccccgggcccacccgcaagcatt
accagccctatgccccaccacgcgacttcgcagcctatcgctcctga SEQ ID NO: 14
MLRLLLALNLFPSIQVTGNKILVKQSPMLVAYDNAVNLSCKYSYNLFSREFRASLHKGLDSA
VEVCVVYGNYSQQLQVYSKTGFNCDGKLGNESVTFYLQNLYVNQTDIYFCKIEVMYPPPYL
DNEKSNGTIIHVKGKHLCPSPLFPGPSKP<u>FWVLVVVGGVLACYSLLVTVAFIIFWV</u>***RSKRSRL
LHSDYMNMTPRRPGPTRKHYQPYAPPRDFAAYRS***

SEQ ID NO: 15
atgtgggtccggcaggtaccctggtcattcacttgggctgtgctgcagttgagctggcaatcagggtggcttctagaggtccccaat
gggccctggaggtccctcaccttctacccagcctggctcacagtgtcagagggagcaaatgccaccttcacctgcagcttgtcca
actggtcggaggatcttatgctgaactggaaccgcctgagtcccagcaaccagactgaaaaacaggccgccttctgtaatggttt
gagccaacccgtccaggatgcccgcttccagatcatacagctgcccaacaggcatgacttccacatgaacatccttgacacacg
gcgcaatgacagtggcatctacctctgtggggccatctccctgcaccccaaggcaaaaatcgaggagagccctggagcagag
ctcgtggtaacagagagaatcctggagacctcaacaagatatcccagcccctcgcccaaaccagaaggccggtttcaaggcat
ggtcattggtatcatgagtgccctagtgggtatccctgtattgctgctgctggcctgggccctagctgtcttctgctcaacaagtatgtc
agaggccagaggagctggaagcaaggacgacactctgaaggaggagccttcagcagcacctgtcccctagtgtggcctatgag
gagctggacttccagggacgagagaagacaccagagctccctaccgcctgtgtgcacacagaatatgccaccattgtcttcact
gaagggctgggtgcctcggccatgggacgtaggggctcagctgatggcctgcagggtcctcggcctccaagacatgaggatgg
acattgttcttggcctctttga SEQ ID NO: 16
MWVRQVPWSFTWAVLQLSWQSGWLLEVPNGPWRSLTFYPAWLTVSEGANATFTCSLSN
WSEDLMLNWNRLSPSNQTEKQAAFCNGLSQPVQDARFQIIQLPNRHDFHMNILDTRRNDS
GIYLCGAISLHPKAKIEESPGAELVVTERILETSTRYPSPSPKPEGRFQGMVIGIMSALVGIPVL CONT. Figure 1

LLLAWALAVFCSTSMSEARGAGSKDDTLKEEPSAAPVPSVAYEELDFQGREKTPELPTACV
HTEYATIVFTEGLGASAMGRRGSADGLQGPRPPRHEDGHCSWPL

SEQ ID NO: 17
atgggaaacaactgttacaacgtggtggtcattgtgctgctgctagtgggctgtgagaaggtgggagccgtgcagaactcctgtga
taactgtcagcctggtactttctgcagaaaatacaatccagtctgcaagagctgccctccaagtaccttctccagcataggtggaca
gccgaactgtaacatctgcagagtgtgtgcaggctatttcaggttcaagaagttttgctcctctacccacaacgcggagtgtgagtg
cattgaaggattccattgcttggggccacagtgcaccagatgtgaaaaggactgcaggcctggccaggagctaacgaagcagg
gttgcaaaacctgtagcttgggaacatttaatgaccagaacggtactggcgtctgtcgaccctggacgaactgctctctagacgga
aggtctgtgcttaagaccgggaccacggagaaggacgtgggaggaccaggagggcactccttgcaggtccttaccttgttcctg
gcgctgacatcggcttaattcccccacatattcaagcaaccatttaagaagaccactggagcagctcaagaggaagatgcttgta
gctgccgatgtccacaggaagaagaaggaggaggaggaggctatgagctgtga SEQ ID NO: 18
MGNNCYNVVVIVLLLVGCEKVGAVQNSCDNCQPGTFCRKYNPVCKSCPPSTFSSIGGQPN
CNICRVCAGYFRFKKFCSSTHNAECECIEGFHCLGPQCTRCEKDCRPGQELTKQGCKTCSL
GTFNDQNGTGVCRPWTNCSLDGRSVLKTGTTEKDVVCGPPVVSFSPSTTISVTPEGGPGG
HSLQVLTLFLALTSALLLALIFITLLFSVLKWIRKKFPHIFKQPFKKTTGAAQEEDACSCRCPQE
EEGGGGGYEL SEQ ID NO: 19
atgacactcaggctgctgttcttggctctcaacttcttctcagttcaagtaacagaaaacaagattttggtaaagcagtcgcccctgct
tgtggtagatagcaacgaggtcagcctcagctgcaggtattcctacaaccttctcgcaaaggaattccgggcatccctgtacaag
ggcgtgaacagcgacgtggaagtctgtgtcgggaatgggaattttacctatcagccccagtttcgctcgaatgccgagttcaactg
cgacggggatttcgacaacgaaacagtgacgttccgtctctggaatctgcacgtcaatcacacagatatttacttctgcaaaattga
gttcatgtaccctccgccttacctagacaacgagaggagcaatggaactattattcacataaaagagaaacatctttgtcatactca
gtcatctcctaagctgttttgggcactggtcgtggttgctggagtcctgttttgttatggcttgctagtgacagtggctctttgtgttatctgg
*acaaatagtagaaggaacagactccttcaagtgactaccatgaacatgactccccggaggcctgggctcactcgaaagccttac*
*cagccctacgcccctgccagagactttgcagcgtaccgcccctga*

SEQ ID NO: 20
MTLRLLFLALNFFSVQVTENKILVKQSPLLVVDSNEVSLSCRYSYNLLAKEFRASLYKGVNSD
VEVCVGNGNFTYQPQFRSNAEFNCDGDFDNETVTFRLWNLHVNHTDIYFCKIEFMYPPPYL
DNERSNGTIIHIKEKHLCHTQSSPKLFWALVVVAGVLFCYGLLVTVALCVIWTNSRRNRLLQV
TTMNMTPRRPGLTRKPYQPYAPARDFAAYRP

CONT. Figure 1

SEQ ID NO: 21

ATGCAGATTCCTCAGGCCCCTTGGCCTGTCGTGTGGGCTGTGCTCCAGCTGGGATGGC
GGCCTGGCTGGTTTCTGGACAGCCCCGACAGACCCTGGAACCCCCCTACATTTTCCCC
TGCCCTGCTGGTCGTGACCGAGGGCGACAATGCCACCTTCACCTGTAGCTTCAGCAAC
ACCAGCGAGAGCTTCGTGCTGAACTGGTACAGAATGAGCCCCAGCAACCAGACCGACA
AGCTGGCCGCCTTCCCCGAGGATAGATCTCAGCCCGGCCAGGACTGCCGGTTCAGAGT
GACCCAGCTGCCCAACGGCCGGGACTTCCACATGTCTGTCGTGCGGGCCAGACGGAA
CGACAGCGGCACATATCTGTGCGGCGCCATCAGCCTGGCCCCCAAGGCCCAGATCAAA
GAGAGCCTGAGAGCCGAGCTGAGAGTGACCGAGAGAAGGGCCGAAGTGCCTACCGCC
CACCCTAGCCCATCTCCAAGACCTGCCGGCCAG<u>ATTATCTCATTCTTCCTGGCCCTGAC
CTCTACCGCCCTGCTGTTTCTGCTGTTCTTTCTGACCCTGCGGTTCAGCGTCGTG</u>***AAGC
GGGGCAGAAAGAAGCTGCTGTACATCTTCAAGCAGCCCTTCATGCGGCCCGTGCAGA
CCACCCAGGAAGAGGACGGCTGCTCCTGCCGGTTTCCCGAGGAAGAAGAGGGGGGC
TGCGAGCTCTAA***

SEQ ID NO: 22

MQIPQAPWPVVWAVLQLGWRPGWFLDSPDRPWNPPTFSPALLVVTEGDNATFTCSFSNT
SESFVLNWYRMSPSNQTDKLAAFPEDRSQPGQDCRFRVTQLPNGRDFHMSVVRARRNDS
GTYLCGAISLAPKAQIKESLRAELRVTERRAEVPTAHPSPSPRPAGQ<u>IISFFLALTSTALLFLLF
FLTLRFSVV</u>*KRGRKKLLYIFKQPFMRPVQTTQEEDGCSCRFPEEEEG*

SEQ ID NO: 23

ATGCAGATTCCTCAGGCTCCTTGGCCTGTCGTGTGGGCCGTGCTCCAGCTGGGATGGC
GGCCTGGATGGTTCCTGGACAGCCCCGACAGACCCTGGAACCCCCCTACATTTTCCCC
TGCCCTGCTGGTCGTGACCGAGGGCGACAATGCCACCTTCACCTGTAGCTTCAGCAAC
ACCAGCGAGAGCTTCGTGCTGAACTGGTACAGAATGAGCCCCAGCAACCAGACCGACA
AGCTGGCCGCCTTCCCCGAGGATAGATCTCAGCCCGGCCAGGACTGCCGGTTCAGAGT
GACCCAGCTGCCCAACGGCCGGGACTTCCACATGTCTGTCGTGCGCGCCAGACGGAA
CGACAGCGGCACATATCTGTGCGGCGCCATCAGCCTGGCCCCCAAGGCCCAGATCAAA
GAGAGCCTGAGAGCCGAGCTGAGAGTGACCGAGAGAAGGGCCGAAGTGCCTACCGCC
CACCCTAGCCCATCTCCAAGACCTGCCGGCCAG<u>TTCCAGACACTGGTCGTGGGAGTCG
TGGGCGGCCTGCTGGGATCTCTGGTGCTGCTCGTGTGGGTGCTGGCCGTGATC</u>***AAGC
GGGGCAGAAAGAAGCTGCTGTACATCTTCAAGCAGCCCTTCATGCGGCCCGTGCAGA
CCACCCAGGAAGAGGACGGCTGCTCCTGCCGGTTTCCCGAGGAAGAAGAGGGGGGC
TGCGAGCTCTAA***

CONT. Figure 1

SEQ ID NO: 24
MQIPQAPWPVVWAVLQLGWRPGWFLDSPDRPWNPPTFSPALLVVTEGDNATFTCSFSNT
SESFVLNWYRMSPSNQTDKLAAFPEDRSQPGQDCRFRVTQLPNGRDFHMSVVRARRNDS
GTYLCGAISLAPKAQIKESLRAELRVTERRAEVPTAHPSPSPRPAGQ<u>FQTLVVGVVGGLLGS
LVLLVWVLAVI</u>*KRGRKKLLYIFKQPFMRPVQTTQEEDGCSCRFPEEEEGGCEL*

SEQ ID NO: 25
ATGCAGATTCCTCAGGCCCCTTGGCCTGTCGTGTGGGCTGTGCTCCAGCTGGGATGGC
GGCCTGGCTGGTTTCTGGACAGCCCCGACAGACCCTGGAACCCCCCTACATTTTCCCC
TGCCCTGCTGGTCGTGACCGAGGGCGACAATGCCACCTTCACCTGTAGCTTCAGCAAC
ACCAGCGAGAGCTTCGTGCTGAACTGGTACAGAATGAGCCCCAGCAACCAGACCGACA
AGCTGGCCGCCTTCCCCGAGGATAGATCTCAGCCCGGCCAGGATTGCCGGTTCAGAGT
GACCCAGCTGCCCAACGGCCGGGACTTCCACATGTCTGTCGTGCGGGCCAGACGGAA
CGACAGCGGCACATATCTGTGCGGCGCCATCAGCCTGGCCCCCAAGGCCCAGATCAAA
GAGAGCCTGAGAGCCGAGCTGAGAGTGACCGAGAGAAGGGCCGAAGTGCCTACCGCC
CACCCTAGCCCATCTCCAAGACCTGCCGGCCAG<u>TTCTGGGTGCTGGTGGTCGTGGGCG
GAGTGCTGGCCTGTTACAGCCTGCTCGTGACCGTGGCCTTCATCATCTTTTGGGTG</u>*CG
CAGCAAGCGGAGCCGGCTGCTGCACAGCGACTACATGAACATGACCCCCAGACGGC
CAGGCCCCACCAGAAAGCACTACCAGCCTTACGCCCCTCCCAGAGACTTCGCCGCCT
ACAGAAGC<u>TGA</u>*

SEQ ID NO: 26
MQIPQAPWPVVWAVLQLGWRPGWFLDSPDRPWNPPTFSPALLVVTEGDNATFTCSFSNT
SESFVLNWYRMSPSNQTDKLAAFPEDRSQPGQDCRFRVTQLPNGRDFHMSVVRARRNDS
GTYLCGAISLAPKAQIKESLRAELRVTERRAEVPTAHPSPSPRPAGQ<u>FWVLVVVGGVLACYS
LLVTVAFIIFWV</u>*RSKRSRLLHSDYMNMTPRRPGPTRKHYQPYAPPRDFAAYRS*

SEQ ID NO: 27
<u>MQIPQAPWPVVWAVLQLGWR</u>MQKGDQNPQIAAHVISEASSKTTSVLQWAEKGYYTMSNN
LVTLENGKQLTVKRQGLYYIYAQVTFCSNREASSQAPFIASLCLKSPGRFERILLRAANTHSS
AKPCGQQSIHLGGVFELQPGASVFVNVTDPSQVSHGTGFTSFGLLKL<u>GGGGSGGGG</u>**DEPK
SCDKTHTCPPCPAPPVAGPSVFLFPPKPKDTLMIARTPEVTCVVVDVSHEDPEVKFNWYV
DGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK**_GPS_<u>KPFWVLVV
VGGVLACYSLLVTVAFIIFWV</u>*RSKRSRLLHSDYMNMTPRRPGPTRKHYQPYAPPRDFAAYR
S*

SEQ ID NO: 28

<u>MQIPQAPWPVVWAVLQLGWR</u>MQKGDQNPQIAAHVISEASSKTTSVLQWAEKGYYTMSNN
LVTLENGKQLTVKRQGLYYIYAQVTFCSNREASSQAPFIASLCLKSPGRFERILLRAANTHSS
AKPCGQQSIHLGGVFELQPGASVFVNVTDPSQVSHGTGFTSFGLLKL<u>GGGGSGGGG</u>DGQ
ACNPSACRAVGRGLQPKGVRVKETADFKVYTKGAGSGELKVTVKGPKGEERVKQKDLG
DGVYGFEYYPMVPGTYIVTITWGGQNIGRSPFEVKV*GPS*<u>KPFWVLVVVGGVLACYSLLVTV</u>
<u>AFIIFWV</u>*RSKRSRLLHSDYMNMTPRRPGPTRKHYQPYAPPRDFAAYRS*

SEQ ID NO: 29

M*RSKRSRLLHSDYMNMTPRRPGPTRKHYQPYAPPRDFAAYRS*ATGLPISMKIFMYLLTVFL
ITQMIGSALFAVYLHRRLDKIEDERNLHEDFVFMKTIQRCNTGERSLSLLNCEEIKSQFEGFV
KDIMLNKEETKKENSFEMQKGDQNPQIAAHVISEASSKTTSVLQWAEKGYYTMSNNLVTLE
NGKQLTVKRQGLYYIYAQVTFCSNREASSQAPFIASLCLKSPGRFERILLRAANTHSSAKPC
GQQSIHLGGVFELQPGASVFVNVTDPSQVSHGTGFTSFGLLKL

SEQ ID NO: 30

*MIETYNQTSPRSAATGLPISMK*<u>IFMYLLTVFLITQMIGSALFAVYL</u>HRRLDKIEDERNLHEDFV
FMKTIQRCNTGERSLSLLNCEEIKSQFEGFVKDIMLNKEETKKENSFEMQKGDQNPQIAAHV
ISEASSKTTSVLQWAEKGYYTMSNNLVTLENGKQLTVKRQGLYYIYAQVTFCSNREASSQA
PFIASLCLKSPGRFERILLRAANTHSSAKPCGQQSIHLGGVFELQPGASVFVNVTDPSQVSH
GTGFTSFGLLKL

FUSION PROTEINS OF PD-1 AND 4-1BB

FIELD OF THE INVENTION

The present invention relates to fusion proteins comprising (a) an extracellular domain containing a polypeptide derived from PD-1 or CD40L at its N-terminus; (b) a transmembrane domain; and (c) an intracellular domain containing a polypeptide derived from 4-1BB or CD28 at its C-terminus. Also, fusion proteins with CD28 at the N-terminus and CD40L at the C-terminus are envisaged. The present invention also relates to nucleic acid molecules encoding such fusion proteins, vectors containing such nucleic acid molecules, and host cells containing such vectors. The present invention further relates to methods for producing such host cells. Finally, the present invention relates to pharmaceutical compositions comprising such fusion proteins, nucleic acid molecules, vectors, and/or host cells, particularly for treating diseases or disorders associated with PD-1/PD-L2 or CD40 binding and/or PD-L1/PD-L2 or CD40 expression such as cancer and chronic viral infection.

BACKGROUND OF THE INVENTION

Adoptive transfer of tumor infiltrating Lymphocytes (TILs) is a promising therapy option against tumors (Rosenberg et al., Science (2015), 348: 62-68). Unfortunately, the isolation of TILs and their expansion is not possible with all tumor entities. Therefore, the concept of genetic engineering of T cells with a transgene T cell receptor (TCR) was developed (Hurwitz et al., Cancer Microenviron (2014), 7: 1-9). Yet, to this date, such T cells show short survival, and lose their function in patients (Janicki et al., Cancer Res (2008), 68: 2993-3000; Bai et al., PNAS USA (2008), 105: 13003-13008; Bendle et al., Cancer Res (2004), 64: 8052-8056; Anderson et al., J Immunol (2007), 178: 1268-1276). Co-stimulation of the TCR signalling cascade with co-stimulatory receptors such as CD28 can enhance proliferation, survival and cytotoxicity of the T cells (Chen et al., Nat Rev Immunol (2013), 13: 227-242). However, as epithelial tumors do not express ligands (CD80/86) of the co-stimulatory receptor CD28 and human effector T cells are themselves negative for such receptors, co-stimulation cannot take place in the conservative way. To provide co-stimulation to the T cells that is independent from this classical way, chimeric co-stimulatory receptors were created. They consist of the extracellular domain of the co-inhibitory receptor PD-1 (also known as CD279) and the signalling domain of CD28 (Ankri et al., J Immunol (2013), 4121-4129; Prosser et al., Mol Immunol (2012), 263-272; WO 2013/019615).

Usually, tumor specific T cell express PD-1 on the surface which then binds to its ligand PD-L1 expressed on tumor cells. This binding results in blocking of TCR-signalling and T cell activation, thus leading to inhibition of the tumor specific T cells. In order to co-stimulate TCR signalling (and, thus, to enhance T cell activation), stimulation of CD28 would be necessary; see above. Chimeric co-stimulatory receptors comprising PD-1 and CD28 domains shall exhibit the relevant functions of both, the extracellular receptor function of PD-1 on the one hand, and the intracellular signalling function of CD28 on the other hand. In such chimeric constructs presented so far (Ankri, loc cit; Prosser, loc cit; WO 2013/019615), the transmembrane domains were taken from the respective signalling molecule.

However, although such constructs have been described to reduce PD-L1 mediated T cell inhibition and to enhance T cell activation, such constructs still leave room for further improvement.

This problem has been addressed by the present invention as described herein and as defined in the claims.

SUMMARY OF THE INVENTION

The present invention relates to a fusion protein comprising
(a) an extracellular domain (ECD) containing a polypeptide derived from PD-1 or CD40L at its N-terminus;
(b) a transmembrane domain (TMD); and
(c) an intracellular domain (ICD) containing a polypeptide derived from 4-1BB or CD28 at its C-terminus.

Preferably, in accordance with the present invention, if the extracellular domain (ECD) contains a polypeptide derived from PD-1 at its N-terminus, the intracellular domain (ICD) contains a polypeptide derived from 4-1BB at its C-terminus and vice versa. Likewise, if the extracellular domain contains a polypeptide derived from CD40L at its N-terminus, the intracellular domain contains a polypeptide derived from CD28 at its C-terminus and vice versa. For fusions proteins with an ECD derived from CD40L and an ICD derived from CD28, it is also possible that the ICD is located N-terminally of the TMD, while the TMD is located at the very C-terminus of the fusion protein; cf. fusion proteins as exemplarily (and non-limiting) shown in FIG. 8. In one embodiment of the present invention, the extracellular domain (a) contains a polypeptide derived from PD-1 at its N-terminus and a polypeptide derived from 4-1BB at its C-terminus.

DETAILED DESCRIPTION OF THE INVENTION

Compared to CD28, 4-1BB (CD137) is a co-stimulatory receptor present on a subset of T cells capable of augmenting TCR signaling. 4-1BB is a member of the tumor necrosis factor receptor (TNFR) superfamily and is absent in naïve T cells but induced following T cell stimulation and differentiation into effector cells (Cheuk at al., Cancer Gene Ther (2004), 11: 215-226). The intracellular domain of 4-1BB contains the QEE motif, which, upon ligation with 4-1BBL, expressed on APCs, recruits TNFR associated factor 2 (TRAF2) (Arch et al., Mol Cell Biol (1998), 18: 558-565; Nam et al., J Immunol (2005), 174: 1898-1905). TRAF2 activates MAPK pathways including ERK and activates nuclear translocation of NFκB (Watts, Annu Rev Immunol (2005), 23: 23-68). It thereby enhances cytokine production and T cell survival. Accordingly, the present invention provides fusion (also termed herein "chimeric") proteins comprising or consisting of the extracellular domain (ECD) of PD-1 and the intracellular signaling domain (ICD) of 4-1BB.

In a further aspect of the present invention, a fusion protein is envisaged which comprises an ICD derived from CD28 at its N-terminus, a fragment of an ICD derived from CD40L, the TMD of CD40L, and the ECD from CD40L at its C-terminus (FIG. 8). In one embodiment of the present invention, the fusion protein comprises or consists of the amino acid sequence shown in SEQ ID NO: 29.

Furthermore, the present invention provides a fusion (chimeric) protein comprising the extracellular domain (ECD) of CD40L and the intracellular signaling domain (ICD) of CD28. Expressed in T cells, it has been surprisingly found in context with the present invention that this chimeric protein exerts dual function when interacting with cells expressing its receptor CD40: In the T cell it is supposed to initiate the co-stimulatory pathway providing survival and enhanced effector activity (cis effect). In the interacting CD40 cells (trans effect), i.e. tumor cells, tumor endothelium it is supposed to cause cell death, and in the case that the interacting cell is an antigen presenting cells it is supposed to be able to induce secretion of cytokines (e.g., IL-12) that further supports T cell activity (FIG. 7).

Generally, in context with the present invention, unless otherwise specified herein, fusion proteins comprising or consisting of the extracellular domain (ECD) derived from PD-1, a transmembrane domain (TMD), and the intracellular domain (ICD) derived from 4-1BB are also referred to herein as "PD-1:4-1BB" or "PD-1:BB". Likewise, fusion proteins comprising or consisting of the extracellular domain (ECD) derived from PD-1, a transmembrane domain (TMD), and the intracellular domain (ICD) derived from CD28 are also referred to herein as "PD-1:CD28". Likewise, fusion proteins comprising or consisting of the extracellular domain (ECD) derived from CD40L, a transmembrane domain (TMD), and the intracellular domain (ICD) derived from CD28 are also referred to as "CD40L:CD28" or "CD28:CD40L" (also referred to herein as "CD40L:CD28i" or "CD40L:CD28i" because of the inversed ICD of CD28; cf. also exemplary fusion protein embodiments as shown as variant 3) in FIG. 7 and evaluated in FIGS. 8 to 11) where the ICD of CD28 forms the N-terminus and the ECD of CD40L forms the C-terminus of the fusion protein. The index "$^{TM}$" or "$^{tm}$" in context with fusion proteins indicate which transmembrane domain is used for the respective construct. For example, "PD-1$^{TM}$:BB" or "PD-1$^{tm}$:BB" means that the fusion protein comprises the transmembrane domain of PD-1, while "PD-1:BB$^{TM}$" or "PD-1:BB$^{tm}$" means the fusion protein comprises the transmembrane domain of 4-1BB. Likewise, "CD28:CD40L$^{tm}$" or "CD40L$^{tm}$:CD28" means that the fusion protein comprises the transmembrane domain of CD40L, while "CD40L:CD28$^{TM}$" or means the fusion protein comprises the transmembrane domain of CD28.

In accordance with the present invention, a fusion protein is provided which comprises the extracellular domain (ECD) of PD-1 or CD40L (e.g., PD-1), a transmembrane domain (TMD), and the intracellular domain (ICD) of 4-1BB. As has been surprisingly found in context with the present invention, T cells expressing such a PD-1:BB fusion protein exhibit increased and earlier proliferation rates compared to T cells expressing PD-1:CD28 fusion proteins as exemplarily shown in human melanoma xenografts. As has also surprisingly found in accordance with the present invention, the CD40L:CD28 fusion proteins expressed on T cells were able to activate B cells (trans effect; FIG. 10) as well as to support T cell functions (cis effect) such as increased IFN-γ secretion (cf. FIG. 11A) and cytotoxicity (FIG. 11B).

That is, as has been found in context with the present invention, a fusion product comprising the ICD of 4-1BB (CD137) exhibits superior effects in form of increased proliferation rates compared to constructs comprising the ICD of CD28 when expressed in T cells, e.g., in human melanoma xenograft.

Accordingly, the ECD of the fusion protein described and provided in context with the present invention having an ECD derived from PD-1 preferably has the function to bind to PD-L1/2 on the surface of tumor cells which express PD-L1 as part of an escape mechanism as known in the art. Upon binding of the ECD of the inventive fusion protein, the ICD of the fusion protein—comprising a polypeptide derived from 4-1BB—preferably acts as activating signalling molecule, thus increasing proliferation of the host cell (e.g., T cell such as CD8$^+$ T cell) and/or cytokine secretion.

Likewise, in accordance with the present invention, the ECD of the fusion protein described and provided in context with the present invention having an ECD derived from CD40L preferably has the function to bind to CD40 on the surface of tumor cells which express CD40 as part of an escape mechanism as known in the art. Upon binding of the ECD of the inventive fusion protein, the ICD of the fusion protein—comprising a polypeptide derived from CD28—preferably acts as activating signalling molecule, thus increasing proliferation and/or survival of the host cell (e.g., T cell such as CD8$^+$ T cell) and/or cytokine secretion and/or cytotoxicity.

The fusion protein provided in accordance with the present invention may further comprise a CD3ζ domain. This may particularly be applicable for cases where the fusion protein is not expressed in a T cell or generally in a TCR negative cell or in cases where TCR and/or CAR are not co-transduced (or generally co-expressed) in the cell expressing the fusion construct of the present invention. The ICD amino acid sequence of CD3ζ can be taken from data base known in the art (NP_932170). Generally, CD3ζ may preferably be introduced after the ICD of the 4-1BB or CD28 protein.

The fusion proteins provided herein may particularly comprise at the N-terminus an ECD containing a polypeptide derived from PD-1, preferably the ECD of PD-1 (e.g., human or murine, preferably human PD-1), or from CD40L. In this context, the term "derived from" particularly means that the polypeptide contained in the ECD comprises at least a part of PD-1 (e.g., human or murine, preferably human PD-1), preferably the ECD of PD-1, or CD40L, respectively. As used herein, the term "derived from" PD-1 or CD40L also allows that up to 0, 1, 2, 3, 4, 5, 6, 7, 8, 9, 10 or more amino acid are substituted, deleted, and/or inserted compared to a native sequence of PD-1 (human or murine, preferably human PD-1) or CD40L, or part thereof (e.g., ECD). For example, if the ECD is derived from CD40L, it is also envisaged in context with the present invention that the ECD derived from CD40L may comprise or consist of the ECD highlighted in SEQ ID NO: 30 of FIG. 1. In one embodiment in this context, it may be the soluble part of CD40L (e.g., amino acids 113-261 of SEQ ID NO: 30; FIG. 8). As will be readily recognized by the skilled person, for the ECD of the fusion protein the signal peptide sequence (as recognizable for those of skill in the art and as also depicted in specific SEQ ID NOs. referred to herein) is usually cut off in the mature protein before, during or after integration of the fusion protein in the membrane. It is also possible in accordance with the present invention that if the ECD is derived from CD40L, the signal peptide may be derived from PD-1 (FIG. 8). That is, when referring to fusion proteins or host cells expressing the fusion proteins as described and provided herein, it is always also encompassed in accordance with the present invention that the ECD of the fusion protein may lack the respective signal peptide.

In one embodiment of the present invention, the fusion protein comprises an ECD containing a polypeptide derived from PD-1 or CD40L comprises an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the ECD of human or murine PD-1, e.g., of human PD-1 as depicted in SEQ ID NO: 2 (with or without the signal peptide as depicted in FIG. 1 for SEQ ID NO: 2) or CD40L (as highlighted in SEQ ID NO: 30 in FIG. 1; as full polypeptide according to SEQ ID NO: 30 or only the soluble fragment (amino acids 113-261 of SEQ ID NO: 30), wherein said fusion protein exhibits PD-L1/2 or CD40 binding affinity, respectively. Such binding affinity may be compared to the binding affinity of native PD-1 (e.g., human PD-1) or CD40L to its respective ligand PD-L1/2 or CD40. In context with the present invention, in order to determine whether a given polypeptide exhibits PD-L1/2 or CD40 binding affinity or not, a polypeptide having a binding affinity to native human PD-L1/2 or CD40 which is as least 0.8-fold, preferably at least 0.9-fold, or more preferably at least 1.0-fold as high compared to binding affinity of native human PD-1 to PD-L1/2 or CD40L to CD40, is considered to exhibit binding affinity to PD-L1/2 or CD40, respectively. In this context, the binding affinity of a given polypeptide to PD-L1/2 or CD40 can be measured by methods known in the art and usually and preferably comprises the measurement of the $K_D$ value (dissociation constant) which is expressed as a molar concentration. Such methods for measuring protein interactions in terms of $K_D$ are well known in the art and comprise, e.g., ELISA, flow cytometry, surface plasmon resonance, biacore measurement, and the like.

In one embodiment of the present invention, the fusion protein comprises an ECD comprising or consisting of the amino acid sequence of the ECD of PD-1 according to SEQ ID NO: 2 (with or without the signal peptide as depicted in FIG. 1 for SEQ ID NO: 2). In another embodiment of the present invention, the fusion protein comprises an ECD comprising or consisting of the amino acid sequence of the ECD of CD40L as highlighted in SEQ ID NO: 30 in FIG. 1 (as full polypeptide according to SEQ ID NO: 30 or only the soluble fragment according to amino acids 113-261 of SEQ ID NO: 30).

The ECD of the fusion protein described and provided herein may further comprise a hinge- and/or a linker region at the C-termimus of the ECD (e.g., between the ECD and TMD of the fusion protein, or between the ECD and the ICD of the fusion protein where the TMD is located C-terminally of the ICD) in order to allow more flexibility to the ECD. Typical hinge- or linker regions are known in the art and comprise those derived from the constant region (Fc) of antibodies (e.g., IgG1, CD8alpha) (see, e.g., Shirasu et al., Anticancer Res (2012), 32: 2377-2383 and Cartellieri et al., J Biomed Biotechnol (2010), 956304) (e.g., IgGFc spacers), Gly/Ser linkers, or filamin (e.g., Fil3 spacers). Yet, as such linker- or hinge regions may also cause side effects due to activation of NK cells which secrete high amounts of inflammatory cytokines, it may be desirable in context with the present invention that the fusion proteins described and provided herein do not comprise linker- or hinge regions. That is, in one embodiment of the present invention, the ECD of the fusion protein does not comprise a linker- or hinge region. In another embodiment, where the ECD is derived from CD40L and the ICD is derived from CD28, there are one or more linker- or hinge regions C-terminally of the ECD, e.g., a Gly/Ser linker plus an Fc spacer (e.g., IgGFc spacer) and/or a filamin linker (e.g., Fil3), e.g. as highlighted accordingly in SEQ ID NOs. 27 or 28 of FIG. 1.

The fusion proteins provided herein further comprise a TMD operably linked between the ECD and the ICD or linked C-terminally of the ICD (e.g. where the ECD is derived from CD40L and the ICD is derived from CD28). Generally, the TMD is not limited to a specific TMD. Preferably, the TMD allows stable anchorage of the fusion protein in the membrane of a cell expressing the fusion protein (e.g., a T cell) and further allows binding of the ECD to PD-L1/2 or CD40, respectively, and, upon binding to PD-L1/2 or CD40, allows signaling induction of the ICD containing a polypeptide derived from 4-1BB, CD28 or CD40L as described and exemplified herein. In context with the present invention, TMDs may inter alia comprise those derived from CD8(alpha), CD28, ICOS, PD-1, or 4-1BB. In one embodiment, if the ECD is derived from CD40L and the ICD is derived from CD28, the TMD is derived from CD28 (CD40L:CD28$^{tm}$) or from CD40L (CD28:CD40L$^{tm}$). For example, the fusion protein comprises or consists of an amino acid sequence shown in SEQ ID NOs 27, 28 or 29. The TMDs may generally be of any origin, but are preferably murine or human, more preferably human.

In one embodiment of the present invention, the TMD of the fusion protein is not derived from CD8(alpha), and/or ICOS. If the ECD is derived from PD-1 and the ICD is derived from 4-1BB, the TMD is in one embodiment also not derived from CD28.

In one embodiment of the present invention, the TMD of the fusion protein comprises a polypeptide derived from PD-1, 4-1BB (e.g., human or murine), particularly where the ECD is from PD-1 and the ICD is from 4-1BB, or the TMD is derived from CD28, particularly where the ECD is from CD40L and the ICD is from CD28 (e.g., as highlighted in SEQ ID NOs: 27 or 28 of FIG. 1). In a specific embodiment of the present invention, the TMD of the fusion protein comprises a polypeptide derived from PD-1, e.g., human or murine PD-1, particularly human PD-1. In this context, the term "derived from" particularly means that the polypeptide contained in the TMD comprises at least a part of PD-1, 4-1BB (e.g., human or murine, preferably human PD-1 or 4-1BB) or CD28, preferably the TMD of PD-1 or 4-1BB (e.g., PD-1), particularly where the ECD is from PD-1 and the ICD is from 4-1BB. As used herein, the term "derived from" PD-1, 4-1BB, or CD28 also allows that up to 0, 1, 2, 3, 4, 5, 6, 7, 8, 9, 10 or more amino acid are substituted, deleted, and/or inserted compared to a native sequence of PD-1, 4-1BB (human or murine, preferably human PD-1 or 4-1BB), or CD28, or part thereof (e.g., TMD).

As has been shown in context with the present invention, fusion proteins having an ICD derived from 4-1BB generally exhibit superior proliferation rates of the host cells (e.g., T cells such as CD8+ T cells) compared to similar constructs having an ICD derived from CD28 and an ECD from PD-1. Furthermore, fusion proteins comprising a TMD derived from PD-1 lead to an even higher secretion rate of cytokines (e.g., IFNγ or IL-2) in transduced T cells compared to fusion proteins comprising a TMD derived from 4-1BB. Accordingly, in a specific embodiment of the present invention, the TMD of the fusion protein comprises or consists of a polypeptide derived from PD-1, e.g., human or murine PD-1, particularly human PD-1.

In one embodiment of the present invention, the fusion protein comprises a TMD containing a polypeptide derived from 4-1BB comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the TMD of human or murine 4-1BB, e.g., of human 4-1BB as depicted SEQ ID NO: 6, wherein said fusion protein is capable of increasing the proliferation rate of a CD8$^+$ T cell when retrovirally transduced into a said CD8$^+$ T cell upon stimulation of said CD8$^+$ T cell with a PD-L1/2$^+$ target cell as described and exemplified herein. Proliferation can be quantified by CFSE dye dilution, i.e. reduction of CFSE fluorescence intensity measured by flow cytometry (as exemplified in FIG. 5 and Method description "Proliferation of TCR-D115 T cells . . . ", or any other suitable method known in the art to determine proliferation, e.g., $H^3$ thymidin incorporation, BrdU incorporation, etc. If the proliferation of the CD8$^+$ T cell retrovirally transduced with the given fusion protein is greater than 1.0, such as at least 1.2-fold, preferably at least 1.3-fold, more preferably at least 1.5-fold higher compared to the CD8$^+$ T cell which was not transduced with the fusion protein, the fusion protein is considered capable of increasing proliferation. Using the CFSE dilution method, the proliferation difference can be calculated as the ratio of mean fluorescence activity (MFI) between T cells without chimeric receptor (mock) and T cells expressing a PD-1:BB or PD-1:CD28 variant. A MFI ratio of 1.0 indicates no difference in proliferation, whereas a MFI ratio of greater than 1.0 indicates proliferation.

In one embodiment of the present invention, the fusion protein comprises a TMD comprising or consisting of the amino acid sequence of the TMD of 4-1BB according to SEQ ID NO: 6, particularly where the ECD is derived from PD-1 and the ICD is derived from 4-1BB.

In one embodiment of the present invention, particularly where the N-terminal ECD is derived from CD40L and the C-terminal ICD is derived from CD28, the fusion protein comprises a TMD (which may be located at the N- or C-terminal of the ICD, preferably at the N-terminal of the ICD) containing a polypeptide derived from CD28 comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the TMD of CD28 as highlighted in SEQ ID NO: 27 or 28 of FIG. 1, wherein said fusion protein is capable of increasing the activation rate of B cells when expressed on TCR-T58 cells as shown in FIG. 10. If the activation increase of the B cell is greater 1.2-fold, preferably at least 1.3-fold, more preferably at least 1.5-fold compared to the B cell activation rate with TCR-T58 cells which were not transduced with the fusion protein, the fusion protein is considered capable of increasing activation.

In another embodiment of the present invention, particularly where the C-terminal ECD is derived from CD40L and the N-terminal ICD is derived from CD28, the fusion protein comprises a TMD (which may preferably be located between the ICD and the ECD) containing a polypeptide derived from CD40L comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the TMD of CD40L as highlighted in SEQ ID NO: 29 of FIG. 1, wherein said fusion protein is capable of increasing the activation rate of B cells when expressed on TCR-T58 cells as shown in FIG. 10. If the activation increase of the B cell-is greater 1.2-fold, preferably at least 1.3-fold, more preferably at least 1.5-fold compared to the B cell activation rate with TCR-T58 cells which were not transduced with the fusion protein, the fusion protein is considered capable of increasing activation.

In one embodiment of the present invention, the fusion protein comprises a TMD containing a polypeptide derived from PD-1 comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the TMD of human or murine PD-1, e.g., of human PD-1 as depicted SEQ ID NO: 8, wherein said fusion protein is capable of increasing secretion of IFNγ and/or IL-2 when retrovirally transduced into a CD8$^+$ T cell upon stimulation of said CD8$^+$ T cell with a PD-L1/2$^+$ target cell. Assessment whether a given fusion protein is capable of increasing secretion of IFNγ and/or IL-2 when retrovirally transduced into a CD8$^+$ T cell upon stimulation of said CD8$^+$ T cell with a PD-L1/2$^+$ target cell can be performed by methods known in the art and as also described and exemplified herein (cf. also "Coculture and cytokine assay" as exemplified herein below). In order to assess whether a given fusion protein is capable of increasing secretion of IFNγ and/or IL-2, the IFNγ and/or IL-2 secretion level of a CD8$^+$ T cell retrovirally transduced with said fusion protein is compared to the IFNγ and/or IL-2 secretion level of a comparable CD8$^+$ T cell not transduced with said fusion protein. For this purpose, both CD8$^+$ T cells (one transduced with the fusion protein, the other one not transduced) are stimulated with a PD-L1/2$^+$ target cell as described and exemplified herein followed by measuring the secretion level of IFNγ and/or IL-2. The CD8$^+$ T cell transduced with the fusion protein and the non-transduced control CD8$^+$ T cell are usually derived from the same donor. For example, transgenic human T cells may be retrovirally transduced to express the fusion protein containing said polypeptide derived from 4-1BB, then cultured with HEK/Tyr or HEK/Tyr/PD-L1 cells at a 1:2 ratio. Co-culture supernatants may then be harvested after 16 h and analyzed by sandwich ELISA (BD) or Bio-Plex (Bio-Rad) according to the manufacturer's protocol. In case the transduced TCRs are only functional in CD8$^+$ T cells and the CD8$^+$/CD4$^+$ T cell ratio varies, the amount of measured cytokine can be normalized to the percentage of TCR$^+$CD8$^+$ T cells within the cell suspension (determined by flow cytometry), applying the following formula:

$$\frac{\text{cytokine produced by}}{100\% \ TCR + CD8 + T \ \text{cells}} = \frac{\text{cytokine concentration measured}}{\% \ TCR + CD8 + T \ \text{cells detected by } FC} \times 100$$

Methods for measuring the secretion level of IFNγ and IL-2 are well known in the art and also exemplified herein and comprise, inter alia, ELISA, Bio-Plex, intracellular flow cytometry (ICS), or the like. If the IFNγ and/or IL-2 secretion level of the CD8$^+$ T cell retrovirally transduced with the given fusion protein is at least 1.2-fold, preferably at least 1.3-fold, more preferably at least 1.5-fold higher compared to the CD8$^+$ T cell which was not transduced with the fusion protein, the fusion protein is considered capable of increasing secretion of IFNγ and/or IL-2.

In one embodiment of the present invention, the fusion protein comprises a TMD comprising or consisting of the amino acid sequence of the TMD of PD-1 according to SEQ ID NO: 8. In another embodiment, particularly where the N-terminal ECD is derived from CD40L and the C-terminal ICD is derived from CD28, the fusion protein comprises a TMD (which may be located at the N- or C-terminal of the ICD, preferably at the N-terminal of the ICD), the TMD comprises or consists of the amino acid sequence of the TMD of CD28 as highlighted in SEQ ID NO: 27 or 28 of FIG. 1. In yet another embodiment of the present invention, particularly where the C-terminal ECD is derived from CD40L and the N-terminal ICD is derived from CD28, the fusion protein comprises a TMD (which may preferably be located between the ICD and the ECD), the TMD comprises or consists of the amino acid sequence of the TMD of CD40L as highlighted in SEQ ID NO: 29 of FIG. 1.

The fusion proteins provided herein further comprise an ICD operably linked to the C-terminus of the TMD (particularly for fusion proteins where the ECD is from PD-1 and the ICD is from 4-1 BB), or operably linked to the C- or N-terminus of the TMD (particularly for fusion proteins where the ECD is from CD40L and the ICD is from CD28). The ICD of the inventive fusion proteins contains a polypeptide which is derived from 4-1BB (CD137) or CD28. In this context, the term "derived from" particularly means that the polypeptide contained in the ICD comprises at least a part of 4-1BB (e.g., human or murine, preferably human 4-1BB), preferably the ICD of (human) 4-1 BB, or CD28. As used herein, the term "derived from" 4-1 BB or CD28 also allows that up to 0, 1, 2, 3, 4, 5, 6, 7, 8, 9, 10 or more amino acid are substituted, deleted, and/or inserted compared to a native sequence of 4-1BB (human or murine, preferably human 4-1BB) or CD28, or part thereof (e.g., ICD). In a specific embodiment of the present invention, the ICD of the fusion protein comprises a polypeptide derived from the ICD of 4-1BB, e.g., human or murine 4-1BB, particularly human 4-1BB. In another embodiment of the present invention, particularly where the ECD is from CD40L and the ICD is from CD28, the fusion protein comprises a polypeptide derived from the ICD of CD28, for example comprising or consisting of an amino acid sequence highlighted in SEQ ID NO: SEQ ID NO: 27, 28, or 29 of FIG. 1 (according to SEQ ID NO: 27 or 28 particularly for cases where the ECD is located at the N-terminus of the fusion protein and the ICD is located at the C-terminus (C- or N-terminally of the TMD, preferably C-terminally of the TMD) of the fusion protein; and according to SEQ ID NO: 29 particularly for cases where the ICD is located at the N-terminus of the fusion protein and the ECD is located at the C-terminus of the fusion protein).

In one embodiment of the present invention, the fusion protein comprises an ICD containing a polypeptide derived from 4-1BB comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the ICD of human or murine 4-1BB, e.g., of human 4-1BB as depicted in SEQ ID NO: 4, wherein said fusion protein is capable of increasing the proliferation rate of a CD8+ T cell when retrovirally transduced into said CD8+ T cell upon stimulation of said CD8+ T cell with a PD-L1/2+ target cell as described and exemplified herein.

In another embodiment of the present invention, the fusion protein comprises an ICD containing a polypeptide derived from CD28 comprising an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of the ICD of CD28 as highlighted in SEQ ID NO: SEQ ID NO: 27, 28, or 29 of FIG. 1 (according to SEQ ID NO: 27 or 28 particularly for cases where the ECD is located at the N-terminus of the fusion protein and the ICD is located at the C-terminus (C- or N-terminally of the TMD, preferably N-terminally of the TMD) of the fusion protein; and according to SEQ ID NO: 29 particularly for cases where the ICD is located at the N-terminus of the fusion protein and the ECD is located at the C-terminus of the fusion protein), wherein said fusion protein is capable of increasing the activation rate of B cells when expressed on TCR-T58 cells as shown in FIG. 10. If the activation increase of the B cell is greater 1.2-fold, preferably at least 1.3-fold, more preferably at least 1.5-fold compared to the B cell activation rate with TCR-T58 cells which were not transduced with the fusion protein, the fusion protein is considered capable of increasing activation.

In one embodiment of the present invention, the fusion protein comprises an ICD comprising or consisting of the amino acid sequence of the ICD of 4-1BB according to SEQ ID NO: 4.

In one embodiment of the present invention, the fusion protein provided and described herein comprises or consists of an ECD derived from PD-1, a TMD derived from 4-1BB, and an ICD derived from 4-1BB. In one embodiment, all domains are derived from corresponding human domains. In a specific embodiment, the fusion protein of the present invention comprises or consists of an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of SEQ ID NO: 22 (with or without the signal peptide as depicted in FIG. 1 for SEQ ID NO: 22), wherein said fusion protein exhibits PD-L1/2 binding affinity as described herein, and wherein said fusion protein is capable of increasing the proliferation rate of a CD8+ T cell when retrovirally transduced into said CD8+ T cell upon stimulation of said CD8+ T cell with a PD-L1/2+ target cell as described and exemplified herein. In a further specific embodiment of the present invention, the fusion protein comprises or consists of an amino acid according to SEQ ID NO: 22 (with or without the signal peptide as depicted in FIG. 1 for SEQ ID NO: 22).

In another embodiment of the present invention, fusion protein provided and described herein comprises or consists of an ECD derived from CD40L, a TMD derived from CD28 or CD40L (CD28 where the ECD is located at the N-terminus of the fusion protein and the ICD is located at the C-terminus (C- or N-terminally of the TMD, preferably N-terminally of the TMD) of the fusion protein; CD40L where the ICD is located at the N-terminus of the fusion protein and the ECD is located at the C-terminus of the fusion protein), and an ICD derived from CD28. In one embodiment, all domains are derived from corresponding human domains. In a specific embodiment, the fusion protein of the present invention comprises or consists of an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of SEQ ID NOs: 27, 28, or 29 (for SEQ ID NOs. 27 and 28: with or without the signal peptide as depicted in FIG. 1 for 27 or 28; for SEQ ID NO: 29: compared to full polypeptide according to SEQ ID NO: 29 or to the soluble fragment thereof according to amino acids 113-261 of SEQ ID NO: 29), wherein said fusion protein exhibits CD40 binding affinity as described herein, and wherein said fusion protein is capable of increasing the activation rate of B cells when expressed on TCR-T58 cells as shown in FIG. 10. In a further specific embodiment of the present invention, the fusion protein comprises or consists of the amino acid sequence of SEQ ID NOs: 27, 28, or 29 (with or without the signal peptide as depicted in FIG. 1 for 27, 28, or 29).

In one embodiment of the present invention, the fusion protein provided and described herein comprises or consists of an ECD derived from PD-1, a TMD derived from PD-1, and an ICD derived from 4-1BB. In one embodiment, all domains are derived from corresponding human domains. In a specific embodiment, the fusion protein of the present invention comprises or consists of an amino acid sequence with up to 0, 1, 2, 3, 4, 5, 6, 7, 8, 9, or 10 amino acid substitutions (preferably conservative or highly conservative substitutions), deletions and/or insertions compared to the amino acid sequence of SEQ ID NO: 24 (with or without the signal peptide as depicted in FIG. 1 for SEQ ID NO: 24), wherein said fusion protein exhibits PD-L1/2 binding affinity as described herein, and wherein said fusion protein is capable of increasing secretion of IFNγ and/or IL-2 when retrovirally transduced into a CD8$^+$ T cell upon stimulation of said CD8$^+$ T cell with a PD-L1/2$^+$ target cell as described and exemplified herein. In this context, in order to assess whether a given fusion protein is capable of increasing the proliferation rate of a $CD8^+$ T cell as well as increasing the IFNγ and/or IL-2 secretion level of said $CD8^+$ T cell retrovirally transduced with said fusion protein is compared to the proliferation rate/the IFNγ and/or IL-2 secretion level of a comparable $CD8^+$ T cell not transduced with said fusion protein. Methods for assessing proliferation and IFNγ/IL-2 secretion rates are known in the art and described and exemplified herein above and below.

In a further specific embodiment of the present invention, the fusion protein comprises or consists of an amino acid according to SEQ ID NO: 24 (with or without the signal peptide as depicted in FIG. 1 for SEQ ID NO: 24).

It must be noted that as used herein, the singular forms “a”, “an”, and “the”, include plural references unless the context clearly indicates otherwise. Thus, for example, reference to “a reagent” includes one or more of such different reagents and reference to “the method” includes reference to equivalent steps and methods known to those of ordinary skill in the art that could be modified or substituted for the methods described herein.

Unless otherwise indicated, the term “at least” preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term “and/or” wherever used herein includes the meaning of “and”, “or” and “all or any other combination of the elements connected by said term”.

The term “about” or “approximately” as used herein means within 20%, preferably within 10%, and more preferably within 5% of a given value or range.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integer or step. When used herein the term “comprising” can be substituted with the term “containing” or “including” or sometimes when used herein with the term “having”.

When used herein “consisting of” excludes any element, step, or ingredient not specified in the claim element. When used herein, “consisting essentially of” does not exclude materials or steps that do not materially affect the basic and novel characteristics of the claim.

In each instance herein any of the terms “comprising”, “consisting essentially of” and “consisting of” may be replaced with either of the other two terms.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer’s specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

As used herein, “conservative” substitutions mean substitutions as listed as “Exemplary Substitutions” in Table 1 below. “Highly conservative” substitutions as used herein mean substitutions as shown under the heading “Preferred Substitutions” in Table I below.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met: ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

The term “polypeptide” is equally used herein with the term “protein”. Proteins (including fragments thereof, preferably biologically active fragments, and peptides, usually having less than 30 amino acids) comprise one or more amino acids coupled to each other via a covalent peptide bond (resulting in a chain of amino acids). The term “polypeptide” as used herein describes a group of molecules which typically comprise more than 10 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms “polypeptide” and “protein” also refer to naturally modified polypeptides/proteins wherein the modification is effected e.g. by post-translational modifications like glycosylation, acetylation, phosphorylation and the like. Such modifications are well known in the art.

The term “amino acid” or “amino acid residue” as used herein typically refers to an amino acid having its art recognized definition such as proteinogenic amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

Generally, as used herein, the term "fusion protein" relates to a protein which is made of polypeptide parts from different sources. Accordingly, it may be also understood as a "chimeric protein", a "chimeric construct", "fusion construct", or the like. Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details to the production of the fusion protein of the present invention are known in the art and described and exemplified herein.

The present invention further relates to a nucleic acid molecule encoding the fusion protein provided and described herein. The present invention also relates to nucleic acid molecules which only encode parts of the fusion protein described and provided herein, e.g., which encode only the ECD, the TMD, and/or the ICD of the fusion protein. For example, the present invention relates to nucleic acid molecules according to SEQ ID NOs. 1, 3, 5, 7, 21, or 23, or combinations thereof linked via nucleic acid bonds, provided a fusion protein according to the present invention or a part thereof (e.g., the ECD, TMD and/or ICD) is encoded. The present invention also relates to nucleic acid molecules where 30, 27, 24, 21, 18, 15, 12, 9, 6, 3, or 0 nucleotides have been substituted (preferably silent mutations which do not result in a change of translated amino acid), deleted or inserted compared to nucleic acid molecules according to SEQ ID NOs. 1, 3, 5, 7, 21, or 23, or combinations thereof linked via nucleic acid bonds, provided a fusion protein according to the present invention or a part thereof (e.g., the ECD, TMD and/or ICD) is encoded. In principle, the present invention preferably relates to nucleic acids encoding fusion proteins specifically described and embodied herein. Generally, SEQ ID NOs. 13 and 14 show the human nucleic acid and amino acid sequence of CD28, respectively, where the predominant transcript of CD28 is depicted. Yet, given that CD28 also exists in further splice variants (e.g., in-frame donor splice variants or variants lacking an in-frame coding exon), such variants or parts thereof (particularly TMD thereof) are also encompassed to be part of the fusion protein described and provided herein. Generally, SEQ ID NOs. 13 and 14 show the human nucleic acid and amino acid sequence of CD28, respectively, where the predominant transcript of CD28 is depicted.

As used herein, unless specifically defined otherwise, the term "nucleic acid" or "nucleic acid molecule" is used synonymously with "oligonucleotide", "nucleic acid strand", "polynucleotide", or the like, and means a polymer comprising one, two, or more nucleotides. The term "nucleic acid molecule" relates to the sequence of bases comprising purine- and pyrimidine bases which are comprised by polynucleotides, whereby said bases represent the primary structure of a nucleic acid molecule. Herein, the term "nucleic acid molecule" includes all kinds of nucleic acid, including DNA, cDNA, genomic DNA, RNA, synthetic forms of DNA and mixed polymers comprising two or more of these molecules, and preferably relates to DNA and cDNA. As readily understood by those of skill in the art, the nucleic acid sequences provided herein represent sequences of DNA and also comprise corresponding RNA sequences where T is replaced by U. The term "nucleic acid molecule" generally comprises sense and antisense strands. "Nucleic acid molecule" may further comprise non-natural or derivatized nucleotide bases as well as natural or artificial nucleotide analogues, e.g., in order to protect the nucleic acid molecule against endo- and/or exonucleases as will be readily appreciated by those skilled in the art.

The present invention further relates to a vector comprising the nucleic acid molecule described and provided herein.

The term "vector" as used herein generally comprises all kinds of linear or circular nucleic acid molecules which can replicate autonomously is a suitable host cell. Such vectors comprise, but are not limited to, plasmids, cosmids, phages, virus (e.g., adeno-, adeno-associated-, lenti-, or preferably retroviral vectors), and other vectors or shuttles known in the art which are suitable to carry and transfer genes into host cells in order to allow stable or transient translation and constitutive or conditional expression of the inventive fusion protein in the host cell. The vector is usually not integrated into the cell genome, but may also be integrated. Vectors according to the present invention which comprise nucleic acid molecules as described and provided herein preferably allow stable expression of the fusion protein of the present invention in the host cell (expression vector). Vectors of the present invention may further comprise marker genes, promoter and/or enhancer sequences (operably linked to the nucleic acid molecule of the present invention), replication origin suitable for the respective host cell, restriction sited, multiple cloning sites, labels and further functional units as known in the art. The vectors may inter alia be transferred into host cells via a shuttle such as a virus (which may itself be considered a vector), or be nakedly transformed or transduced into host cells. The vector is preferably adapted to suit to the respective host cell where it is to be transformed or transduced into. The skilled person will readily understand that different host cells will require different kinds of vectors. For example, as shown herein the vector (plasmid) pGEM is a suitable vector for transformation into bacterial cells, while the retroviral vector pMP71 is suitable for transduction into eukaryotic cells (e.g., T cells).

In one embodiment of the present invention, the vector of the present invention is a viral vector, e.g., a retroviral or lentiviral vector, e.g., a retroviral vector. Examples for suitable retroviral vectors are known in the art and include, e.g., pMP71-PRE (Leisegang, K Mol Med (2008), 86(5): 573-583), SAMEN CMVISRa, LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sei. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7

(1996), 1123-1129), pGIXsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sei. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In a specific embodiment of the present invention, the vector is pMP71-PRE or pMP71.

The present invention further relates to a host cell comprising the nucleic acid molecule or the vector as described and provided herein. In one embodiment, the host cell of the present invention is transduced or transformed with the nucleic acid molecule or the vector as described and provided herein.

Generally, as used herein unless specifically defined otherwise, the terms "transduced" or "transformed" (as well as "transduction" or "transformation") or the like may be used interchangeably and generally mean any kind of transfer of a nucleic acid molecule and/or vector into a host cell, regardless of the kind of host cell and regardless of the way of transfer (e.g., (chemical) transformation, (viral) transduction, electroporation, transfection, etc.). The nucleic acid molecule and/or the vector may be stably integrated into the genome of the host cell, or be extrachromosomal (i.e. transient expression). Examples for suitable methods for achieving transient expression in a host cell are known in the art and comprise mRNA transfection. In one embodiment, the nucleic acid molecule and/or the vector is stably integrated into the genome.

The host cell described and provided in context with the present invention comprising the nucleic acid molecule or the vector as described and provided herein is preferably able to stably or transiently (e.g., stably) express (either constitutively or conditionally) the fusion protein of the present invention. The host cell may generally be transduced or transformed by any method with any suitable nucleic acid molecule or vector. In one embodiment, the host cell is transduced with a retroviral or lentiviral (e.g., retroviral) vector comprising a nucleic acid molecule encoding the fusion protein of the present invention or parts thereof (e.g., ECD, TMD, and/or ICD) as described above.

In one embodiment, the host cell of the present invention is transduced with a retroviral vector comprising a nucleic acid molecule encoding the fusion protein of the present invention or parts thereof (e.g., ECD, TMD, and/or ICD) as described above and stably expresses (either constitutively or conditionally) the fusion protein or part thereof. Preferably, the host cell then stably expresses the fusion protein in its membrane, with the ECD of the fusion protein of the present invention directed to the surface, the TMD being (largely) embedded in the membrane, and the ICD directed to the cytoplasm.

In context with the present, the host cell comprising the nucleic acid molecule or the vector as described and provided herein relates to a genetically modified cell where said nucleic acid molecule or said vector was transduced, transformed or otherwise introduced into the host cell. As already mentioned, the host cell of the present invention may be a cell which transiently or stably expresses the fusion protein of the present invention. For example, the nucleic acid molecule encoding the fusion protein of the present invention can be stably integrated into the genome of the cell by retroviral or lentiviral (e.g., retroviral) transduction. The PD-1-BB fusion protein is expressed in the membrane of the herein provided transduced cell. The ECD of the PD-1 part of the fusion protein located on the cell surface, while the TMD and ICD intracellular are bound to the membrane but are not detectable on the cell surface. The detection of the ECD of the PD-1 polypeptide can be carried out by using an antibody or other binding molecule specifically binding the ECD of PD-1 as described herein, e.g., by ELISA or by flow cytometry, or microscopy. The transduced cell of the present invention may be, e.g., $CD8^+$ T cells, $CD4^+$ T cells, double-negative $\alpha/\beta$ T cells, NK (natural killer) cells, $\gamma\delta$ T cells, macrophages, dendritic cells, as well as cells suitable store and/or reproduce the nucleic acid molecule or vector of the present invention, including bacterial cells (e.g., E. coli) and further eukaryotes. In one embodiment, the host cell of the present invention is a T cell, e.g., a $CD8^+$ T cell.

The host cell of the present invention may be transduced with a nucleic acid molecule or a vector encoding the fusion protein as described and provided herein. Preferably, the host cell provided and described herein may be co-transduced with further nucleic acid molecules, e.g. with a nucleic acid molecule encoding a T cell receptor (TCR) or a chimeric antigen receptor (CAR). Such co-transduction (or other method for introducing nucleic acid molecules into cells as described and exemplified herein) is known in the art and also described and exemplified herein.

Examples of suitable host cells according to the present invention include, but are not limited to, T cells, e.g. $CD8^+$ T cells, $CD4^+$ T cells, TCR such as (but not limited to) TCR-T58 or TCR-D115 T cells, double-negative $\alpha/\beta$ T cells, NK (natural killer) cells, $\gamma\delta$ T cells, macrophages, dendritic cells, as well as cells suitable store and/or reproduce the nucleic acid molecule or vector of the present invention, including bacterial cells (e.g., E. coli) and further eukaryotes. The cells may be autologous or non-autologous, but are preferably autologous.

Also, the cells may be allogeneic or non-allogeneic as readily clear for the skilled person. In one embodiment, the host cell of the present invention is a $CD8^+$ T cell.

The present invention also relates to a method of preparing a host cell of the present invention as described and provided herein, said method comprising
(1) transducing or transforming a host cell as described above with a nucleic acid molecule or a vector as described and provided herein;
(2) cultivating the transduced host cell of step (1) in a suitable medium allowing growth of the cell and expression of the fusion protein encoded by said nucleic acid molecule or said vector; and
(3) collecting the host cells from the medium.

In a preferred embodiment of the present invention, the host cell is transduced or transformed outside the human body. Methods for obtaining, isolating and culturing cells (e.g., T cells such as $CD8^+$ T cells, $CD4^+$ T cells, TCR such as (but not limited to) TCR-T58 or TCR-D115 T cells) from donors (e.g., human donors) are known in the art and comprise inter alia blood draw or bone marrow removal.

In accordance with the method of the present invention, the host cell may be transduced or transformed or otherwise be provided with a nucleic acid molecule or a vector as described and provided herein by any method known in the art. Such methods comprise, inter alia, (chemical) transformation, (viral) transduction, electroporation, transfection, and the like. In one embodiment, the host cell is transduced with a retroviral vector.

The host cell to be prepared in accordance with the present invention may be any host cell as described herein. In one embodiment, the host cell is a T cell, for example a CD8$^+$ T cell, CD4$^+$ T cell, TCR such as (but not limited to) TCR-T58 or TCR-D115 T cell.

The present invention also relates to a host cell obtainable by the preparation method provided herein.

The present invention further relates to a pharmaceutical composition comprising a fusion protein, a nucleic acid molecule, a vector, and/or a host cell as described and provided by the present invention. Such pharmaceutical composition is suitable to be administered to patient (preferably, human patient), particularly to the donor of the host cells as described above. Accordingly, the present invention also relates to methods for treating a disease or disorder by administering comprising a pharmaceutical composition comprising a fusion protein, a nucleic acid molecule, a vector, and/or a host cell as described and provided by the present invention.

The pharmaceutical composition of the present invention may further comprise a pharmaceutically acceptable carrier and further components, e.g., for galenic. The pharmaceutical composition is particularly useful for treating diseases or disorders associated with the expression of PD-1 ligands (e.g., PD-L1 or PD-L2) and/or CD40. Such diseases and disorders are known to the skilled person and comprise particularly (but not limited to) different types of cancer such as lung cancer, gastric cancer, renal cell cancer, colon cancer, breast cancer, ovarian cancer, urothelial cancer, melanoma, pancreatic cancer, myeloma, Hodkin's lymphoma, retinoblastoma, leukemia, cervical cancer, esophageal cancer, glioma, non-Hodkin's lymphoma, hepatocellular cancer, oral cancer, and others. Further diseases and disorders which may be treated by the pharmaceutical compositions provided herein comprise (chronic) viral infections and (chronic) inflammations, particularly for cases where PD-L1/L2 and/or CD40 is expressed.

The present invention further relates to a kit or kit-in-parts comprising a fusion protein, a nucleic acid molecule, a vector, and/or a host cell as described and provided in context with the present invention.

The present invention further relates to the following items:

(1) A fusion protein comprising
  (a) an extracellular domain containing a polypeptide derived from PD-1 at its N-terminus;
  (b) a transmembrane domain; and
  (c) an intracellular domain containing a polypeptide derived from 4-1BB at its C-terminus.
(2). The fusion protein of item 1, wherein said transmembrane domain comprises a polypeptide derived from PD-1 or 4-1BB, preferably from PD-1.
(3) The fusion protein of any one of the preceding items, further comprising a CD3 domain.
(4) The fusion protein of any one of the preceding items, wherein said extracellular domain does not comprise a linker or a hinge domain.
(5) The fusion protein of any one of the preceding items, wherein said polypeptide derived from PD-1 comprised by said extracellular and/or by said transmembrane domain is a polypeptide derived from human PD-1.
(6) The fusion protein of any one of the preceding items, wherein said polypeptide derived from 4-1BB comprised by said transmembrane and/or by said intracellular domain is a polypeptide derived from human 4-1BB.
(7) The fusion protein of any one of the preceding items, wherein said extracellular domain containing a polypeptide derived from PD-1 comprises an amino acid sequence with 0, 1, 2, 3, 4, 5, 6, 7, 8, 9, or 10 amino acid substitutions, deletions, and/or insertions compared to the amino acid sequence of SEQ ID NO: 2,
  wherein said fusion protein exhibits PD-L1/2 binding affinity.
(8) The fusion protein of any one of the preceding items, wherein said intracellular domain containing a polypeptide derived from 4-1BB comprises an amino acid sequence with 0, 1, 2, 3, 4, 5, 6, 7, 8, 9, or 10 amino acid substitutions, deletions, and/or insertions compared to the amino acid sequence of SEQ ID NO: 4,
  wherein said fusion protein is capable of increasing the proliferation rate of a CD8$^+$ T cell when retrovirally transduced into a said CD8$^+$ T cell upon stimulation of said CD8$^+$ T cell with a PD-L1/2$^+$ target cell.
(9) The fusion protein of any one of items 2 to 8, wherein said transmembrane domain containing a polypeptide derived from PD-1 comprises an amino acid sequence with 0, 1, 2, 3, 4, 5, 6, 7, 8, 9, or 10 amino acid substitutions, deletions, and/or insertions compared to the amino acid sequence of SEQ ID NO: 8,
  wherein said fusion protein is capable of increasing secretion of IFNγ and/or IL-2 when retrovirally transduced into a CD8$^+$ T-cell upon stimulation of said CD8$^+$ T-cell with a PD-L1/2$^+$ target cell.
(10) The fusion protein of any one of the preceding items, wherein said extracellular domain comprises the amino acid sequence of SEQ ID NO: 2.
(11) The fusion protein of any one of the preceding items, wherein said intracellular domain comprises the amino acid sequence of SEQ ID NO: 4.
(12) The fusion protein of any one of the preceding items, wherein said transmembrane domain comprises the amino acid sequence of SEQ ID NO: 8.
(13) A nucleic acid molecule encoding the fusion protein of any one of the preceding items.
(14) A vector comprising the nucleic acid molecule of item 13.
(15) A host cell comprising the nucleic acid molecule of item 13 or the vector of item 14.
(16) The host cell of item 15 which is transduced with the nucleic acid molecule of item 13 or the vector of item 14.
(17) The host cell of item 15 or 16, wherein said nucleic acid molecule or said vector is stably integrated into the genome of the host cell.
(18) The host cell of item 16 or 17 which is transduced via retroviral transduction.
(19) The host cell of any one of items 15 to 18 stably expressing a fusion protein encoded by the nucleic acid molecule of item 13.
(20) The host cell of any one of items 15 to 19 which is a CD8+ T-cell.
(21) A method of preparing a host cell of any one of items 15 to 20 comprising
  (1) transducing a host cell with a nucleic acid molecule of item 13 or a vector of item 14;
  (2) cultivating the transduced host cell of step (1) in a suitable medium allowing growth of the cell and expression of the fusion protein encoded by said nucleic acid molecule or said vector; and (3) collecting the host cells from the medium.
(22) A host cell obtainable by the method of item 21.
(23) A pharmaceutical composition comprising a fusion protein of any one of items 1 to 12, a nucleic acid molecule of item 13, a vector of item 14, and/or a host cell of any one of items 15 to 20 or 22.
(24) The fusion protein of any one of items 1 to 12, the nucleic acid molecule of item 13, the vector of item 14, the host cell of any one of items 15 to 20 or 22, or the pharmaceutical composition of item 23 for use in treating cancer and chronic viral infection.
(25) A kit or kit-in-parts comprising a fusion protein of any one of items 1 to 12, a nucleic acid molecule of item 13, a vector of item 14, and/or a host cell of any one of items 15 to 20 or 22.

BRIEF DESCRIPTION OF THE DRAWINGS

General legend for sequences unless specified otherwise:
Bold: signal peptide (usually cut off in mature protein); Underlined: TMD; Italics and Bold: ICD; CAPITAL LETTERS for nucleotide sequences: codon-optimized sequences
FIG. 1: SEQ ID NO 1: nucleic acid sequence ECD human PD-1
SEQ ID NO: 2: amino acid sequence ECD human PD-1
SEQ ID NO: 3: nucleic acid sequence ICD human 4-1BB
SEQ ID NO: 4: amino acid sequence ICD human 4-1BB
SEQ ID NO: 5: nucleic acid sequence TMD human 4-1BB
SEQ ID NO: 6: amino acid sequence TMD human 4-1BB
SEQ ID NO: 7: nucleic acid sequence TMD human PD-1
SEQ ID NO: 8: amino acid sequence TMD human PD-1
SEQ ID NO: 9: nucleic acid sequence human PD-1
SEQ ID NO: 10: amino acid sequence human PD-1
SEQ ID NO: 11: nucleic acid sequence human 4-1BB
SEQ ID NO: 12: amino acid sequence human 4-1BB
SEQ ID NO: 13: nucleic acid sequence human CD28
SEQ ID NO: 14: amino acid sequence human CD28
SEQ ID NO: 15: nucleic acid sequence murine PD-1
SEQ ID NO: 16: amino acid sequence murine PD-1
SEQ ID NO: 17: nucleic acid sequence murine 4-1BB
SEQ ID NO: 18: amino acid sequence murine 4-1BB
SEQ ID NO: 19: nucleic acid sequence murine CD28
SEQ ID NO: 20: amino acid sequence murine CD28
SEQ ID NO: 21: nucleic acid sequence human PD-1: $BB^{TM}$
SEQ ID NO: 22: amino acid sequence human PD-1:$BB^{TM}$
SEQ ID NO: 23: nucleic acid sequence human PD-1$^{TM}$:BB
SEQ ID NO: 24: amino acid sequence human PD-1$^{TM}$:BB
EQ ID NO: 25: nucleic acid sequence human PD-1:$CD28^{TM}$
SEQ ID NO: 26: amino acid sequence human PD-1:$CD28^{TM}$
SEQ ID NO: 27: amino acid sequence CD40L:$CD28^{tm}$ with Gly/Ser (G/S) linker and IgGFc spacer:
  PD1SP (signal peptide from PD-1, first underlined sequence part)
  ECD from CD40L (aa 113-261 from SEQ ID NO: 30)
  GS-linker (second underlined sequence part)
  IgGFc (spacer in bold)
  CD28TM (third underlined sequence part)
  ICD from CD28 (aa 148-220, bold italics)
SEQ ID NO: 28: amino acid sequence CD40L:$CD28^{tm}$ with Gly/Ser (G/S) linker and Fil3 spacer:
  PD1SP (signal peptide from PD-1, first underlined sequence part)
  ECD from CD40L (aa 113-261 261 from SEQ ID NO: 30)
  GS-linker (second underlined sequence part)
  Fil3 (spacer in bold)
  CD28TM (third underlined sequence part)
  *ICD* from CD28 (aa 148-220, bold italics)
SEQ ID NO: 29: CD28:$CD40L^{tm}$ with inverted CD28 ICD at N-terminus, short CD40 ICD-fragment, TMD from CD40L and ECD from CD40L at C-terminus
  CD40L (aa 14-261 of SEQ ID NO: 30)
  CD28ICD inverted (bold italics; aa 180-220)
SEQ ID NO: 30: native CD40L sequence
  ICD (bold italics)
  TM (underlined)
  ECD

2 upper lines (green) for TCR-D115/PD-1$^{tm}$:BB
2 center lines (red) for TCR-D115/PD-1:CD28$^{tm}$
2 lower lines (blue) for TCR-D115/mock (control)

Figure 2:
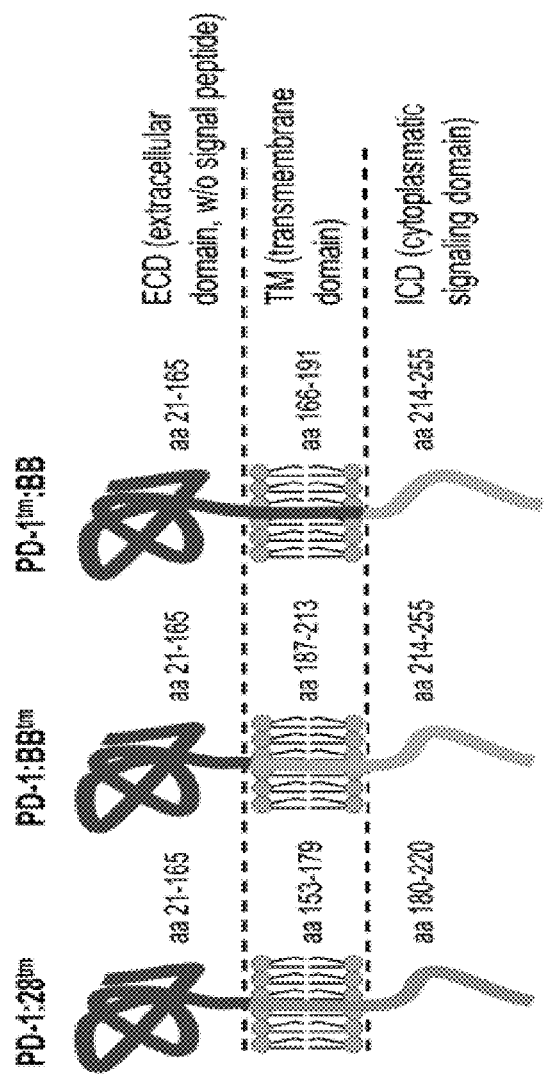
FIG. 2: Design of chimeric PD-1 co-stimulatory receptors
amino acids (aa) correspond to the respective human parental proteins. Note that for the PD-1 ECD, the signal peptide sequence is removed and thus the mature protein is depicted
Figure 3:
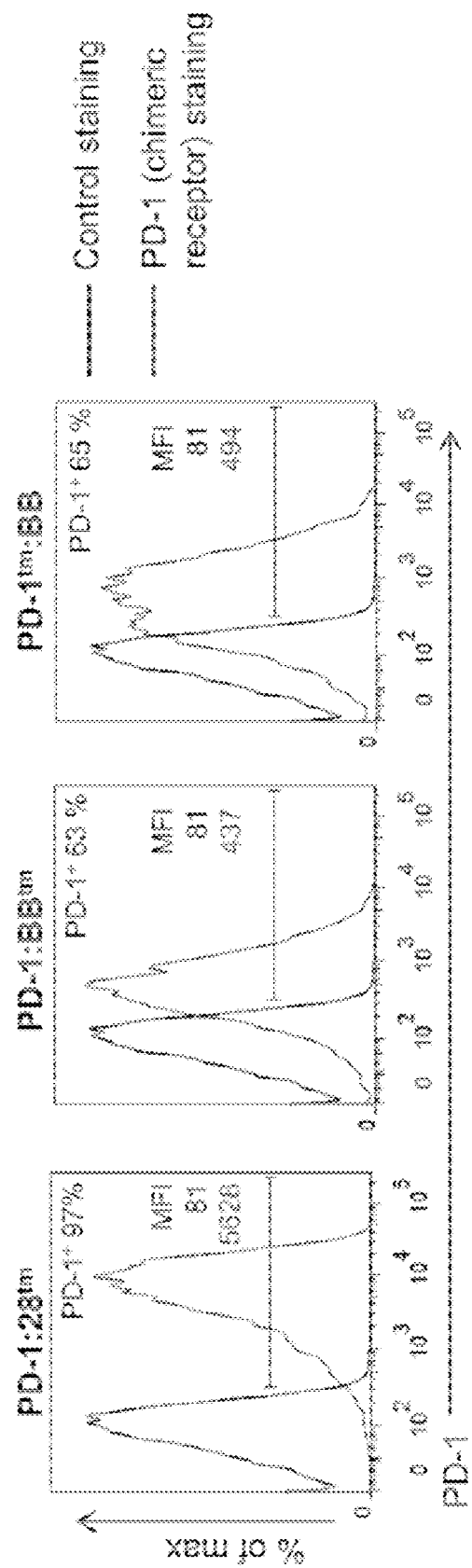
FIG. 3: Chimeric receptor expression on TCR-T58+ CD8+ T cells after retroviral transduction
Human T cells, which stably express the HLA-A2 restricted tyrosinase-specific T cell receptor TCR-T58, were retrovirally transduced with vectors encoding indicated chimeric receptors. T cells were frozen 15 days after transduction for later use. Receptor expression on the T cell surface was evaluated by flow cytometry after defrosting T cells and before T cells were used in co-culture experiments (3 days culture in medium containing 50 U/ml IL-2). Shown are representative FACS histograms demonstrating surface expression of PD-1:$28^{tm}$, PD-1:$BB^{tm}$ and PD-$1^{tm}$:BB as determined by anti-PD-1 staining. Numbers are the % of receptor-positive cells and the corresponding MFI. Black line histograms and black numbers correspond to isotype staining, red line histograms and red numbers correspond to the PD-1 staining.
Figure 4:
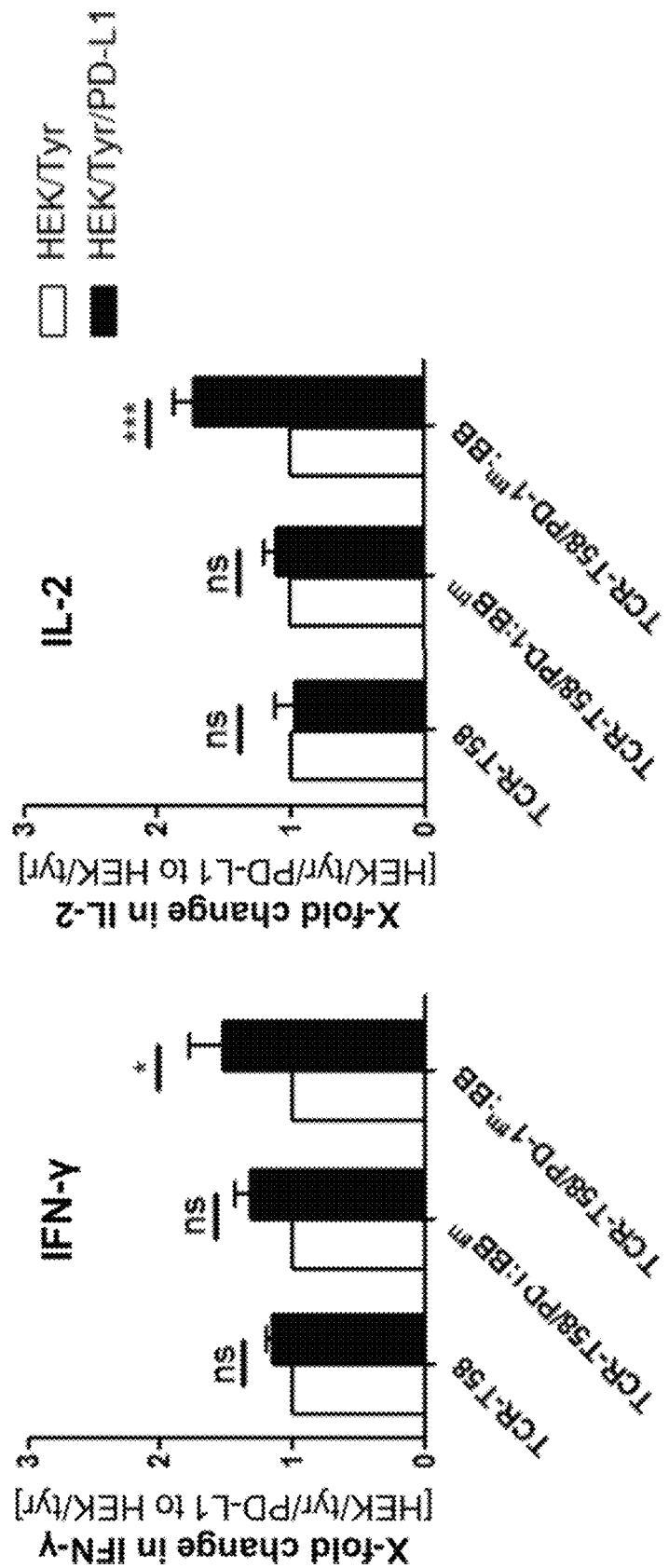
FIG. 4: Effect of chimeric receptors on TCR-induced cytokine secretion
TCR-T58+ T cells which expressed indicated chimeric receptors (see FIG. 3) were co-cultured with (HEK/tyr) or HEK/tyr/PD-L1 for 16 hours. Supernatants were removed and the content of IFNγ and IL-2 was determined by ELISA. Graphics represent the effect of chimeric receptor expression on IFNγ (left) and IL-2 (right) secretion. For each experiment, the x-fold change in cytokine between co-cultures with HEK/tyr and HEK/tyr/PD-L1 was calculated. From all performed experiments (n=2-3), the mean of the x-fold change was determined and presented as bar diagram. Error bars are the SEM. Statistical analysis employed the two-factorial analysis of variance (acc to Sidak). * $p<0.02$ * $p<0.0002$; ** $p<0.0001$; ns=not significant
Figure 5:
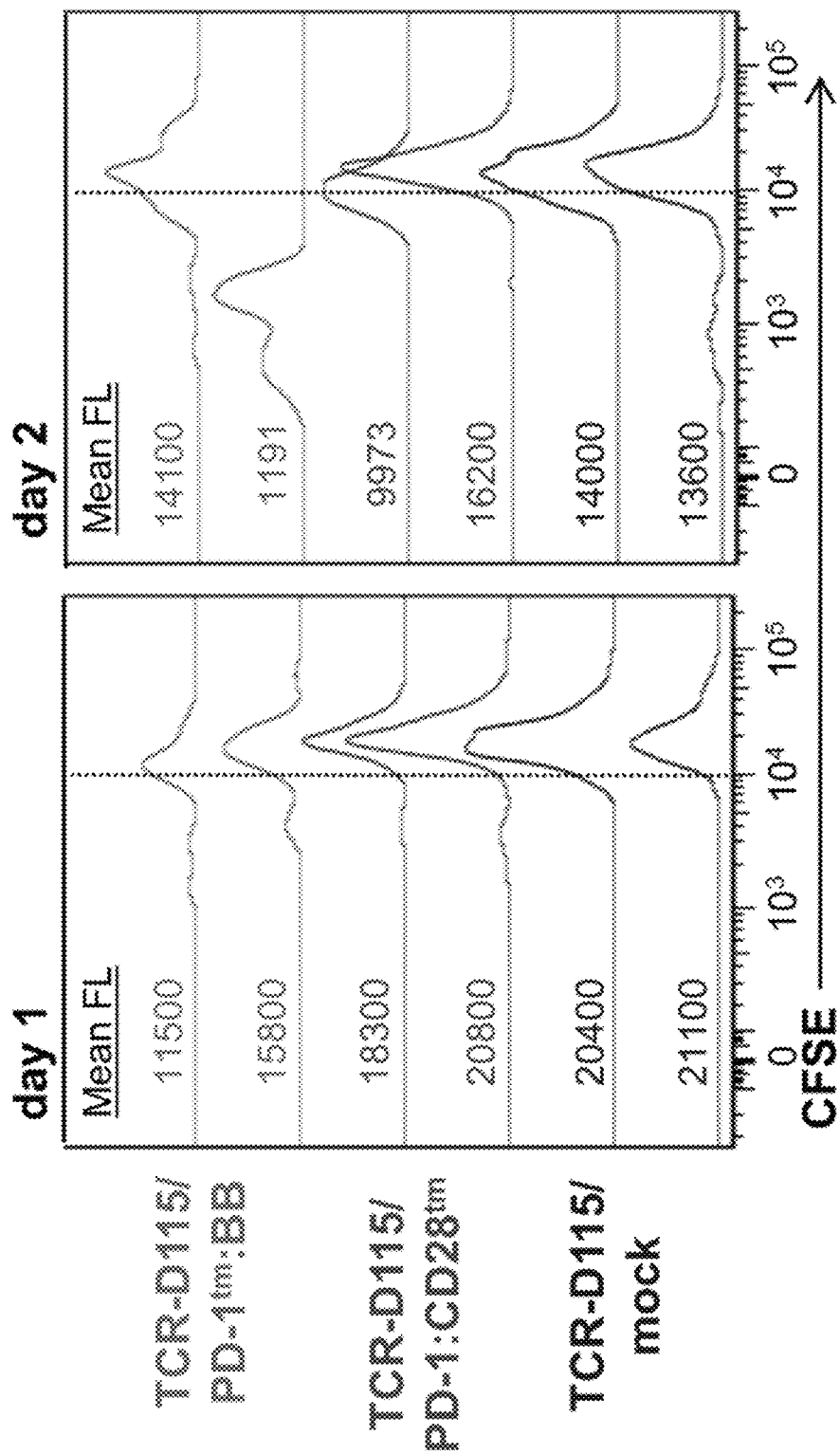
FIG. 5: Effect of chimeric receptors on T cell proliferation in the milieu of human melanoma xenografts in NSG mice
SK-Me123 human melanoma cells expressing the peptide-MHC complex (pMHC) for TCR-D115 T cells (HLA-A2/tyrosinase) were injected s.c. into the flank of immuno-deficient NSG mice. CFSE-labelled TCR-T58$^+$ T cells without co-receptor expression (Mock transduced) and those expressing the chimeric receptor PD-1$^{tm}$:BB or PD-1:$CD28^{tm}$, respectively, were injected intratumorally into established xenografts (802 mm3, SEM±83, ca. 17 days). 1 day, 2 days, 4 days, 6 days and 11 days after T cell injection tumors were harvested, dissociated into single cell suspension and used for flow cytometry. CFSE staining intensity was assessed on T cells (CD8⁺, CD4⁺ and CD4⁻CD8⁻ double-negative (dbl⁻) cells) as a means to determine their proliferative history in the tumor milieu. TCR-D115⁺ CD8⁺ T cells can be activated by the tumor cells and acquire a dbl⁻ phenotype due to activation. CD8⁺ and dbl⁻ T cells demonstrated comparable CFSE dilution and are represented as one population. CD4⁺ T cells cannot recognize the melanoma cells and, therefore, cannot undergo pMHC-specific proliferation. CFSE dilution in CD4⁺ T cells was not seen until 6 days after T cell injection and most likely occurred due to cytokines produced by the activated CD8⁺ T cells (not shown). Shown are representative histograms of CFSE stainings of CD8⁺/dbl⁻ T cells after 1 day and 2 days of i.t. injection. Each histogram corresponds to one tumor of one mouse. Numbers indicate mean fluorescence intensity of CFSE. Vertical line indicates the original CSFE intensity indicative for cells that had not yet started to proliferate. It was observed that on day 1 and day 2, CD8⁺/dbl⁻ T cells that co-expressed the chimeric receptor PD-1$^{tm}$:BB had lower CFSE intensity compared to CD8⁺/dbl⁻ T cells without chimeric receptor or expressing the PD-1:CD28$^{tm}$ receptor, respectively. On day 4, CD8⁺dbl⁻ T cells displayed comparable CFSE dilution independent of chimeric receptor expression (not shown). The early dilution of CFSE by PD-1$^{tm}$:BB expressing T cells indicates that these T cells reacted with the tumor cells more strongly and initiated proliferation earlier than T cells without chimeric receptor or T cells expressing the chimeric receptor PD-1:CD28$^{tm}$.
Figure 6:
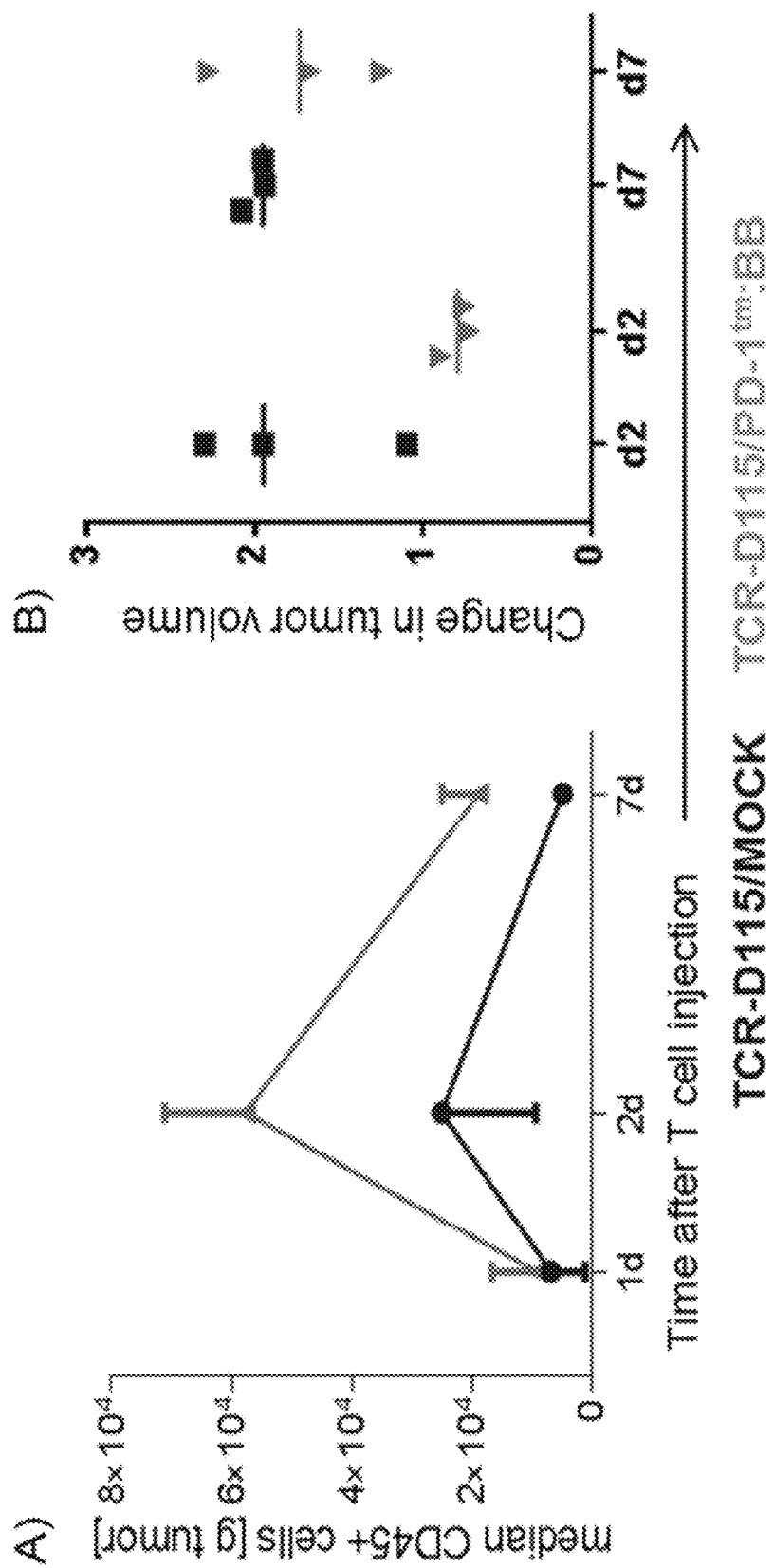

FIG. 6: SK-Me123 human melanoma cells expressing the peptide-MHC complex (pMHC) for TCR-D115 and TCR-T58 T cells (HLA-A2/tyrosinase) were injected s.c. into the flank of immuno-deficient NSG mice. CFSE-labelled TCR-D115 T cells without co-receptor expression (Mock) and those expressing the chimeric receptor PD-1$^{tm}$:BB were injected intratumorally into established xenografts (802 mm3, SEM±83, ca. 17 days). Tumor volume was measured before T cell injection and on day 2 and 7 after injection using caliper: Tumor volume was calculated using the modified ellipsoid formula; volume=(length×width²)×0.52. Mice were sacrificed and tumors were dissociated into single cell suspension and T cells per tumor were counted by for flow cytometry (CD45+ cells (g tumor). N=3 mice per time point and T cell. As shown in A) TCR-D115/PD-1$^{tm}$:BB T cells reached much higher intratumoral cell numbers on day 2 than T cells without chimeric receptor, and numbers were still elevated at day 7. Concomitantly with higher cell numbers, TCR-D115/PD-1$^{tm}$:BB T cells achieved good tumor control with reduction in tumor volume compared to starting volume at day 2, and still better tumor control at day 7 (mean fold-change in tumor volume of 1.7 compared to 2 at day 7) (B).

Figure 7:
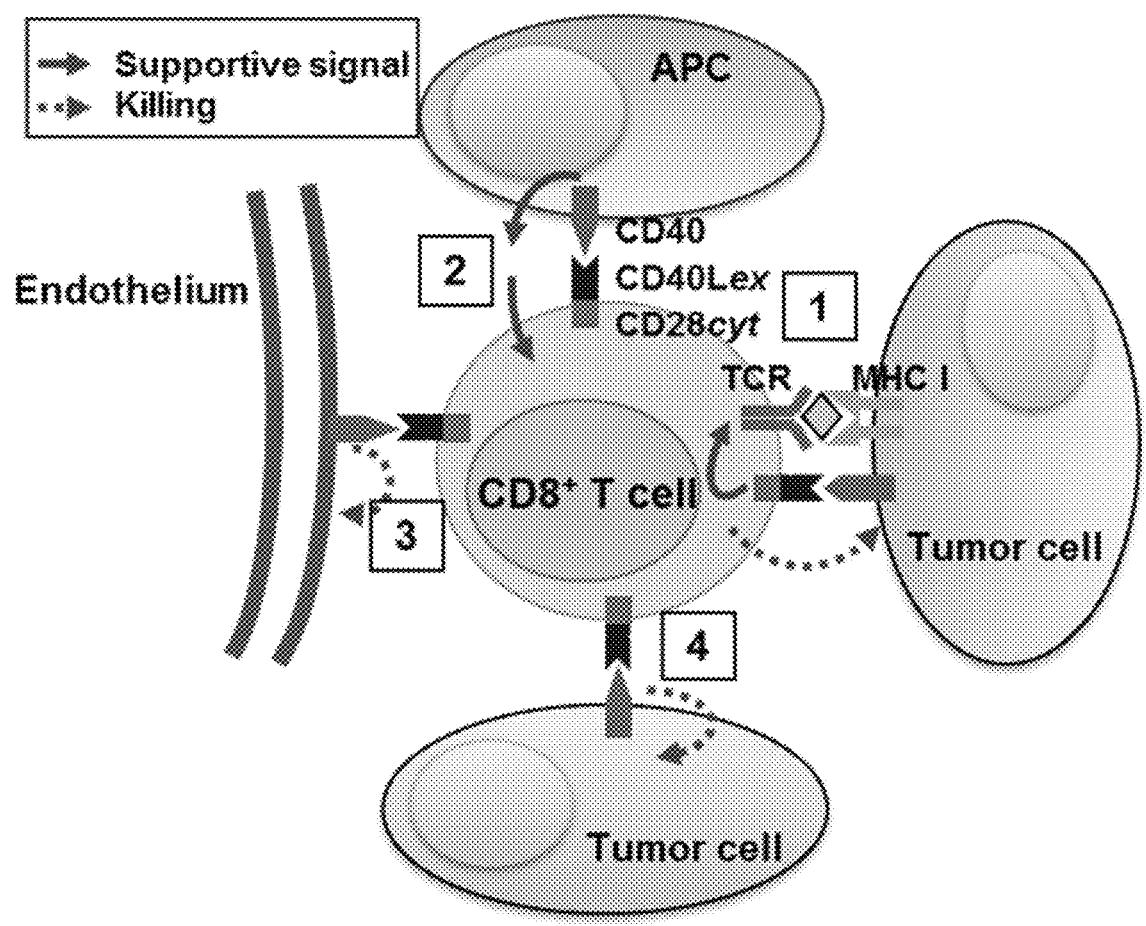

FIG. 7: Projected effects of CD40L:28 chimeric proteins expressed in human T cells.
1) cis-activity-supportive effect on transgene-expressing T cells: Ligation of the fusion protein on T cells induces CD28 signaling and thus supports TCR signals, CTL effector function, and survival, leading to better tumor killing. 2) trans-effect on antigen presenting cells (APC): CD40 activation on APCs will stimulate APC to secrete cytokines (IL-12) and chemokines that will enhance CTL effector function. 3) trans-effect on endothelium: ligation of CD40 expressed on tumor endothelium will cause endothelial apoptosis, thus destroying the tumor's vascular support. 4) trans-effect on tumor cells: ligation of CD40 expressed on tumor cells will cause tumor cell apoptosis.

Figure 8:
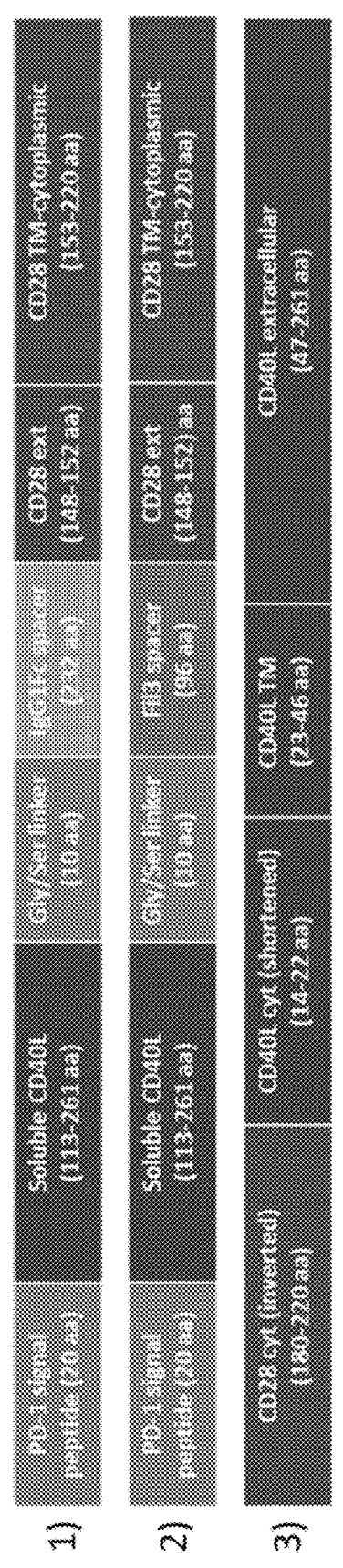
Figure 9:
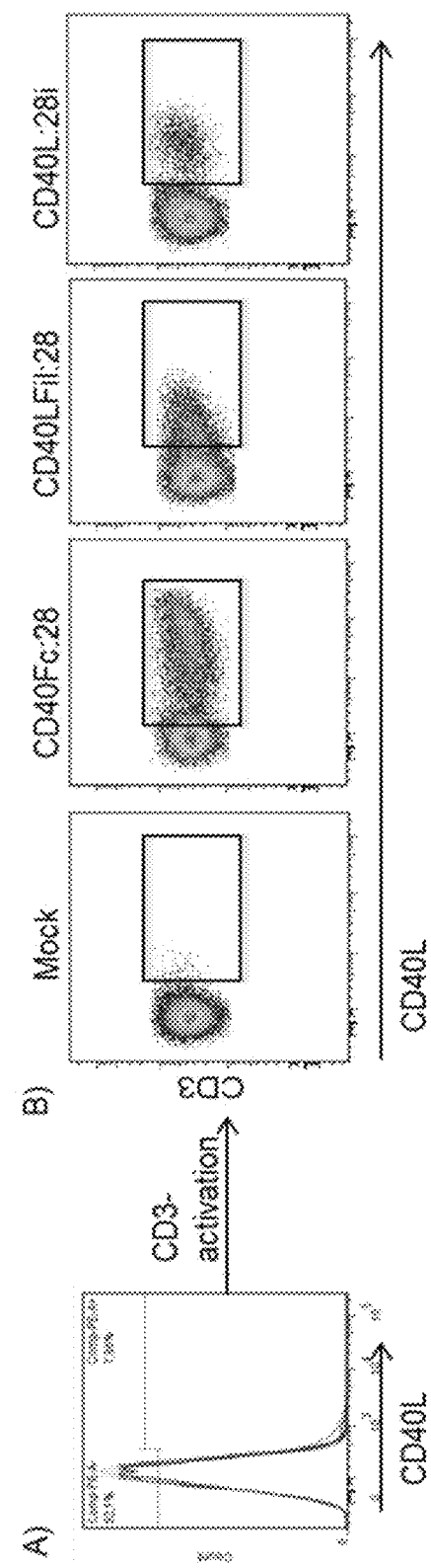

FIG. 8: 3 different constructs are created with different linker and orientation of the domains.
1) CD40LFc:28; 2) CD40LFil:28; 3) CD40L:28i FIG. 9: Expression characteristics of CD40L:28 constructs on human T cells after stable retroviral transduction.

Human T cells were transduced retrovirally to express the chimeric proteins, and surface protein expression was analyzed on day 7 and day 17. While surface expression was detected on day 7, expression vanished until day 17 concomitant with T cells reaching a resting state (FIG. 9A). Surface expression was again achieved after TCR-specific activation (FIG. 9B). Thus, these chimeric proteins exhibit inducible surface presence in a manner that fits with when and where the T cell support is required.

Figure 10:
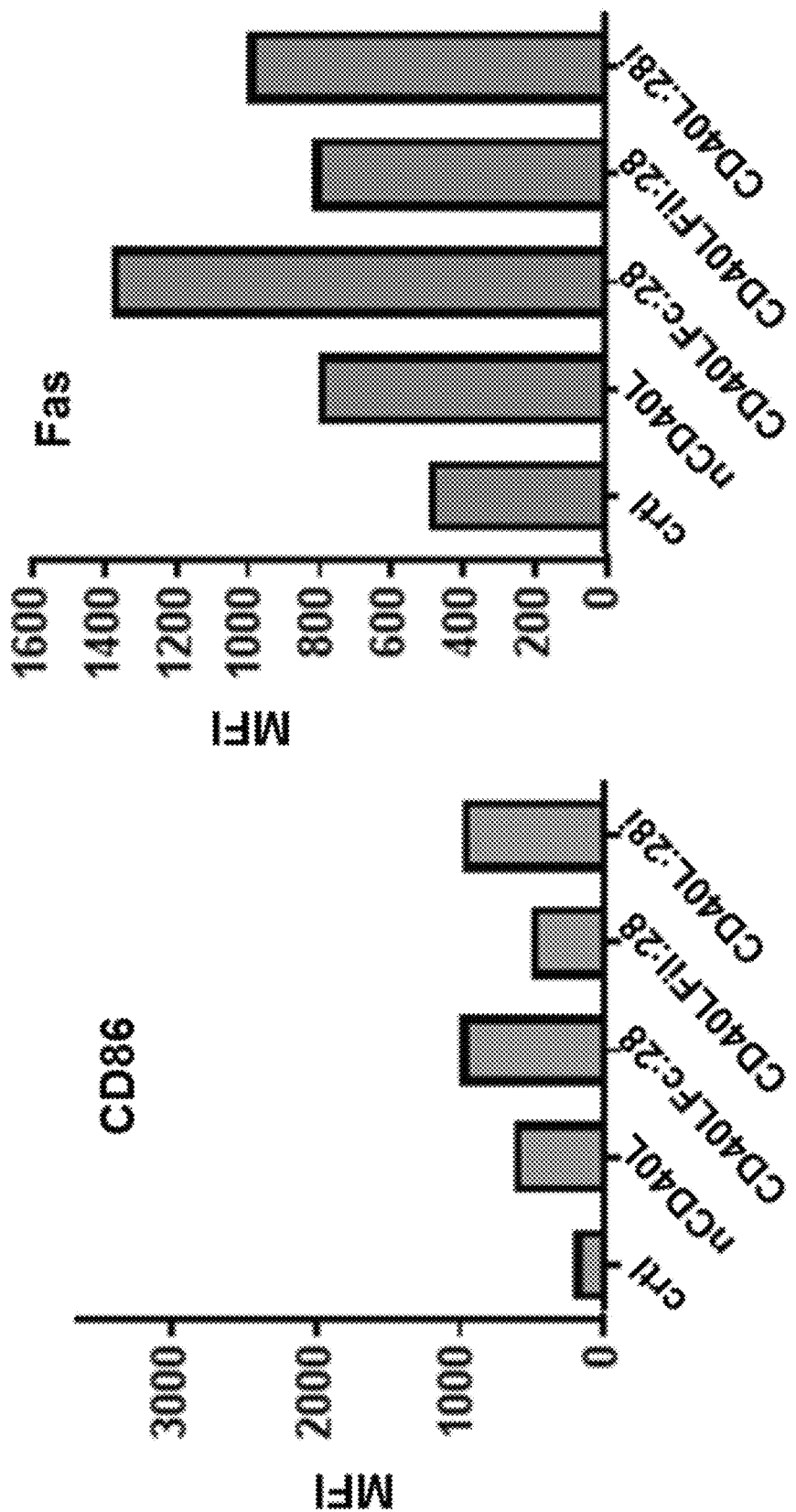

FIG. 10: Chimeric CD40L:28 proteins expressed on T cells can activate B cells (trans-effect).

T cells were co-cultured with primary B cells at 1:1 ratio for 24 h. Thereafter, cells were harvested and analyzed for CD86 and Fas by flow cytometry. Bars depict the mean fluorescence intensity of analyzed marker on B cells. The CD40L-ECD of the chimeric proteins was functionally active as demonstrated by observed higher CD86 and Fas expression on B cells. Similar effect was seen for CD83, another marker of B cell activation (not shown). The 3 different constructs showed graded activity, similar or higher than the native CD40L protein.

Figure 11:
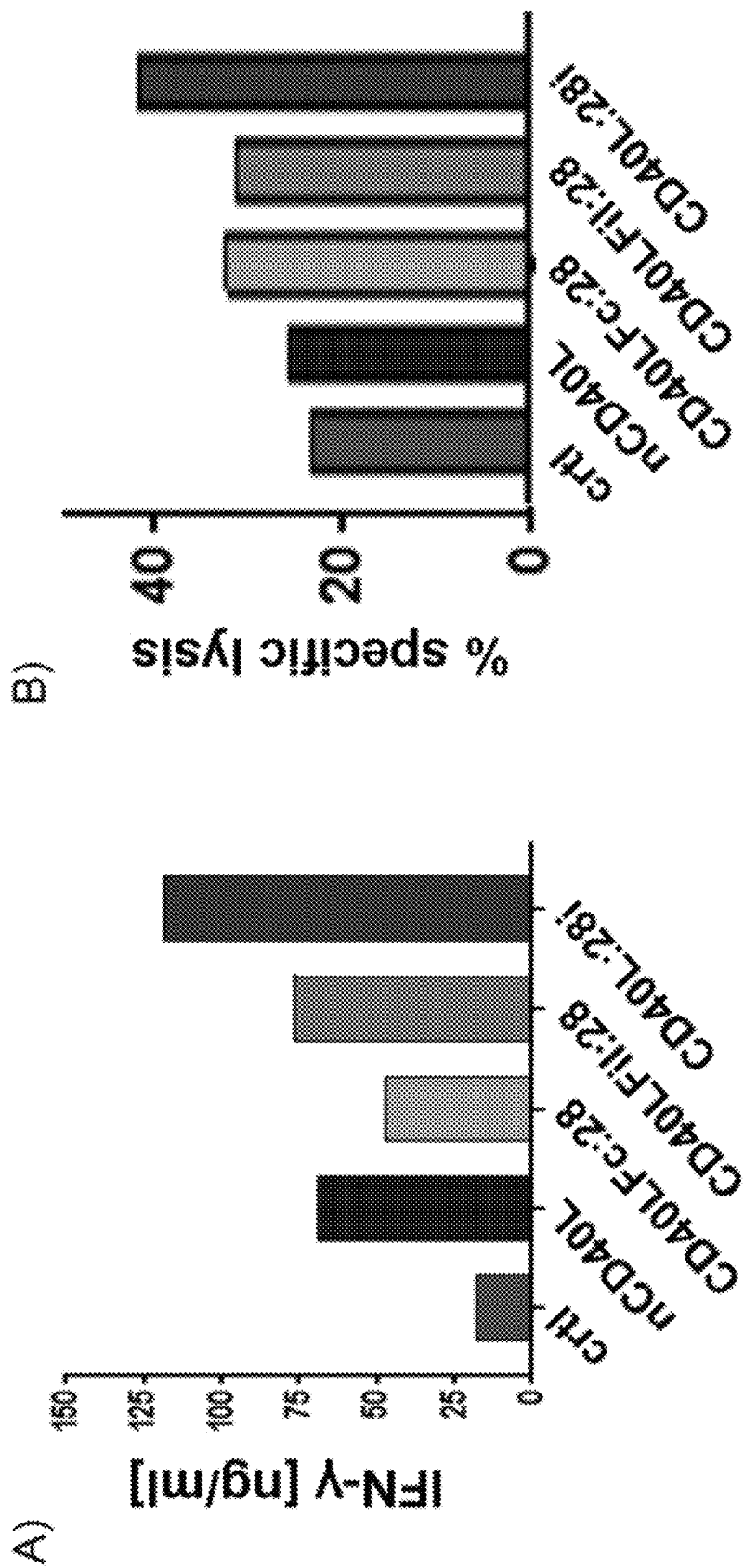

FIG. 11: Chimeric CD40L:28 proteins expressed on TCR-T58 T cells support T cell function (cis-effect).

TCR-T58 transgenic T cells without chimeric protein (crtl) or TCR-T58 transgenic T cells expressing native CD40L or chimeric proteins after retroviral transduction were co-cultured with melanoma cell lines (SK-Mel23, FM86, positive for the TCR ligand and CD40). A) IFN-γ was measured in 48 h co-culture supernatants. B) Cytotoxicity against melanoma tumor cells was measured after 4 h of co-culture (chromium release assay). Depicted results are from 5:1 effector:target ratio. As can be seen in both assays, T cells expressing the chimeric proteins secreted more IFN-γ and exhibited higher cytotoxicity against the tumor cells compared to ctrl. Thus, the CD28-ICD of the chimeric proteins is functionally active, i.e. enhancing effector activity of chimeric protein expressing T cells.

The present invention is further illustrated by the following examples. Yet, the examples and specific embodiments described therein must not be construed as limiting the invention to such specific embodiments

EXAMPLES

Plasmids Encoding Chimeric Receptors

Chimeric receptor sequences were ordered at Geneart, Life Technologies. They were delivered as a lyophilized powder and dissolved in nuclease-free water at a concentration of 0.5 µg/µl. For amplification TOP10 or MACH1 E.coli were chemically transformed with the Geneart constructs, following standard plasmid preparation methods.

Electroporation of Human Primary T Cells with ivtRNA

Chimeric receptor sequences were cloned into pGEM for ivtRNA preparation. Cloning into the pGEM vector (provided by S. Milosevic, Medigene GmbH, Martinsried, Germany) was achieved using HindIII or HindII and EcoRI (New England Biolabs). IvtRNA was generated from pGEM plasmids using the mMESSAGEmMACHINE Kit (Ambion) according to the manufacturer's protocol. Human primary T cells were electroporated with 20 µg ivtRNA at 900 V for 2.3 ms using Gene Pulser Xcell (Bio-Rad).

Retroviral Transduction of Human Primary T Cells

Chimeric receptor sequences were cloned into pMP71-PRE vector (Leisegang 2008, loc. Cit, for retroviral transduction). Retroviral transduction of T cells was achieved as described (Leisegang 2008, loc. cit.). Human PBMCs from healthy donors were plated into 24-well plates at a cell density of 1×106/ml per well in RPM11640 supplemented with 10% human serum, 1% L-glutamine, 1% non-essential amino acids, 1% sodium pyruvate and 1% penicillin/streptomycin (all Invitrogen) plus 100 U/ml IL-2 (Cancernova) and activated with 5 µg/ml OKT3 (provided by E. Kremmer, Helmholtz Center Munich, Germany) and 1 µg/ml anti-CD28 (BD Pharmingen) for 2 days.

Amphotrophic chimeric receptor-encoding retroviruses were generated as described (Leisegang at al., Clin Cancer Res (2010), 16(8): 2333-2343) using TransIT®-LT1 Reagent (Mirus) according to the manufacturer's protocol. Virus supernatant was harvested after 48 h and bound to RetroNectin® (10 µg/ml, Takara) coated plates by centrifugation.

PBMCs, which were activated for 2 days, were added to virus-coated plates for 24 h, then split to freshly virus-coated plates and cultivated for another 3 days. Transduced PBMCs were transferred to uncoated plates and cultivated for at least 12 additional days reducing the amount of IL-2 to 50 U/ml. Receptor expression was determined at day 12 after transduction using anti-PD-1 antibody (BioLegend).

Cell Cultures

HEK/Tyr and HEK/Tyr/PD-L1 were generated by transducing HLA-A2+ HEK293 cells to express tyrosinase (HEK/Tyr) or tyrosinase and PD-L1 (HEK/Tyr/PD-L1). After transduction, HEK293 cells were single-cell cloned and clones selected for comparable HLA-A2 and tyrosinase expression. SK-Me123 (gift from M. C. Panelli, NIH, Bethesda, USA), HEK/Tyr and HEK/Tyr/PD-L1 were grown in RPMI-1640 supplemented with 1% L-glutamine, 1% non-essential amino acids, 1% sodium pyruvate, 1% penicillin/streptomycin (RMPI basic) plus 12% FCS.

Multi-Parameter Flow Cytometry to Determine Chimeric Receptor Expression and T Cell Proliferation Flow cytometry analysis was performed on a LSRII (BD). Cells were stained in PBS (Invitrogen) supplemented with 2% human serum, 0.1% sodium azide and 2 mM EDTA (both Sigma-Aldrich). Expression of human chimeric receptors and transgenic TCRs was analyzed using anti-CD3-PE-Cy7, anti-mouse TCRß-constant region-PB (both BioLegend), anti-CD4-APC-A780, anti-PD-1-APC (both eBioscience), anti-CD8-V500 (BD) and 7-AAD (Sigma-Aldrich).

HEK293 cells were analyzed using anti-HLA-A2 (ATCC HB54) plus anti-mouse IgG1-A488 (Invitrogen), anti-PD-L1-FITC (BD), anti-tyrosinase (Upstate) plus anti-mouse IgG2a-A647 (Invitrogen) and 7-AAD.

T cells after injection into xenograft tumors were analyzed using CFSE, anti-CD45-PE-Cy7, anti-CD8-PB (BD), CD4-APC-A780, anti-PD-1-APC and 7-AAD. CD45+ leukocytes were selected and CFSE intensity was analyzed in $CD8^+$, $CD4^+$ and dbl− cells after gating on viable and single cells. Data were analyzed using FlowJo 8.8.7 software.

Co-cultures and cytokine assays to assess effects of fusion proteins on T cells TCR-T58 or TCR-D115 transgenic human T cells were electroporated with ivtRNA or transduced with retroviral vectors to express chimeric receptors, then cultured with HEK/Tyr or HEK/Tyr/PD-L1 cells at a 1:2 ratio. Co-culture supernatants were harvested after 16 h and analyzed by sandwich ELISA (BD) or Bio-Plex (Bio-Rad) according to the manufacturer's protocol.

Since the transduced TCRs T58 and D115 are only functional in $CD8^+$ T cells and the $CD8^+/CD4^+$ T cell ratio varied between experiments, the amount of measured cytokine was normalized to the percentage of $TCR^+CD8^+$ T cells within the cell suspension (determined by flow cytometry). The following formula was applied:

NSG Mice

NSG mice were obtained from Charles River. NOD/scid IL2Rgnull (NSG) mice were bred on the genetic background of non-obese diabetic (NOD) mice characterized by reduced innate immunity. NSG mice carry the prkdcscid mutation, a loss-of-function mutation in the PRKDC gene, leading to defective repair of DNA strand breaks during V(D)J recombination in the development of B and T cells. This severe combined immunodeficiency (scid) is characterized by a major reduction of T and B cells. Additionally, NSG mice carry a null mutation in the IL-2 receptor gamma chain (IL2Rgnull) blocking NK cell differentiation. The impairment of innate immunity and absence of adaptive immunity render NSG mice a good model system for adoptive T cell therapy of human tumor xenografts.

Human Melanoma Xenograft Model

Animal experiments were approved by the local authorities and performed according to the legal regulations. 7-11 weeks old, male mice were injected s.c. with 5×106 HLA-A2+ tyrosinase+ human melanoma cells SK-Me123 (gift of Monica C. Panelli, NIH, Bethesda, USA). This melanoma line was selected because it expresses PD-L1/L2 as well as HLA-A2 and tyrosinase, which are required to form the ligand for TCR-D115 and TCR-T58 (Wilde et al., Blood (2009), 114: 2131-2139). T cells expressing TCR-D115 were selected for the mouse experiment as they can recognize SK-Mel23 with low avidity which is not sufficient to eradicate established tumors.

Tumors were grown for about 16 days until they reached a size of 802 $mm^3$ (SEM=±83). Tumor size ($mm^3$) was calculated using the formula for determining ellipsoid volumes: $\pi/6 \times length \times width \times height$.

Proliferation of TCR-D115 T Cells in the Tumor Milieu of Human SK-Mel23 Xenografts Cell tracer dyes, i.e CFDA-SE, are used to assess cell proliferation. They permeate cell membranes and are converted to fluorescent carboxyfluorescein succinimidyl esters (i.e. CFSE). With each cell division the fluorescence intensity of CFSE is halved allowing monitoring of T cell proliferation.

Here, TCR-D115 T cells without or with chimeric receptor expression were labeled with 0.15 µM CFDA-SE for 8 minutes at 37° C. The reaction was stopped with FCS, T cells were washed twice with PBS and re-suspended in PBS at a concentration of 10×107 cells per ml. 50 µl of T cell suspension were injected i.t. into established s.c. SK-Mel23 xenografts (802 $mm^3$, SEM=±83).

Tumors were harvested 1, 2, 4, 6 and 11 days after i.t. injection. Single cell suspensions were prepared by mechanical and enzymatic digestion (Prinz et al., J Immunol (2012), 188: 5990-6000) and used for flow cytometry analysis.

Chromium Release Assay $^{51}$Cr-labeled melanoma cells were used as targets at a constant cell number of 2000 cells per well in 96-well V-bottom plates. Experiments were performed with duplicate measurements of four-step titrations of effector cells. In parallel wells, target cells were incubated without T cells to determine the spontaneous release of [51Cr]. Supernatants were harvested after 4 h and transferred to counting plates (PerkinElmer) for cpm measurements. The maximal cpm was determined by directly transferring labeled target cells to the counting for cpm measurements. The percent of specific lysis was calculated as follows: % specific lysis= (experimental cpm−spontaneous cpm)/(maximal cpm−spontaneous cpm)×100.

Statistics

Statistical tests, as indicated in the figure legends, were performed using GraphPad Prism 6 software.

Results

Results are shown in the Figures.

The invention claimed is:

1. A fusion protein comprising
   (a) an extracellular domain of PD-1 consisting of an amino acid sequence with 0, 1, 2, 3, 4, 5, 6, 7, 8, 9, or 10 amino acid substitutions, deletions, and/or insertions compared to the amino acid sequence of SEQ ID NO: 2;
   (b) a PD-1 transmembrane domain consisting of an amino acid sequence SEQ ID NO:8; and
   (c) an intracellular domain of 4-1 BB consisting of an amino acid sequence with 0, 1, 2, 3, 4, 5, 6, 7, 8, 9, or 10 amino acid substitutions, deletions, and/or insertions compared to the amino acid sequence of SEQ ID NO: 4.

2. The fusion protein of claim 1, further comprising a CD3ζ intracellular domain.

3. The fusion protein of claim 1, wherein said extracellular domain consists of the amino acid sequence of SEQ ID NO: 2.

4. The fusion protein of claim 1, wherein said intracellular domain consists of the amino acid sequence of SEQ ID NO: 4.

5. A nucleic acid molecule encoding the fusion protein of claim 1.

6. A vector comprising the nucleic acid molecule of claim 5.

7. A host cell comprising
   (i) a nucleic acid molecule encoding a fusion protein comprising:
      (a) an extracellular domain of PD-1 consisting of an amino acid sequence with 0, 1, 2, 3, 4, 5, 6, 7, 8, 9, or 10 amino acid substitutions, deletions, and/or insertions compared to the amino acid sequence of SEQ ID NO: 2;
      (b) a PD-1 transmembrane domain consisting of SEQ ID NO:8; and
      (c) an intracellular domain of 4-1 BB consisting of an amino acid sequence with 0, 1, 2, 3, 4, 5, 6, 7, 8, 9, or 10 amino acid substitutions, deletions, and/or insertions compared to the amino acid sequence of SEQ ID NO: 4, or
   (ii) a vector comprising said nucleic acid molecule.

8. The host cell of claim 7 stably expressing a fusion protein encoded by said nucleic acid molecule.

9. The host cell of claim 7 which is a CD8$^+$ T-cell.

10. A method of preparing a host cell of claim 7 comprising
    (1) transducing a host cell with said nucleic acid molecule or said vector;
    (2) cultivating the transduced host cell of step (1) in a suitable medium allowing growth of the cell and expression of the fusion protein encoded by said nucleic acid molecule or said vector; and
    (3) collecting the host cells from the medium.

11. A pharmaceutical composition comprising a fusion protein of claim 1, a nucleic acid molecule encoding said fusion protein, a vector comprising said nucleic acid molecule, and/or a host cell comprising said nucleic acid molecule or said vector.

12. A method for treating cancer comprising administering to a patient a host cell comprising a nucleic acid molecule encoding the fusion protein of claim 1 or a vector comprising said nucleic acid molecule, or a pharmaceutical composition thereof.

13. The fusion protein of claim 1, wherein said intracellular domain of 4-1 BB consists of an amino acid sequence with 0, 1, 2, 3, 4, 5, 6, 7, 8, 9, or 10 amino acid substitutions, deletions, and/or insertions compared to the amino acid sequence of SEQ ID NO: 4, wherein said fusion protein is capable of increasing the proliferation rate of a CD8$^+$ T cell when transduced, transformed or otherwise introduced into a said CD8$^+$ T cell upon stimulation of said CD8$^+$ T cell with a PD-L1/L2$^+$ target cell.

14. The fusion protein of claim 1, wherein said PD-1 transmembrane domain consists of SEQ ID NO: 8, wherein said fusion protein is capable of increasing secretion of IFNγ and/or IL-2 when transduced, transformed or otherwise introduced into a CD8$^+$ T-cell upon stimulation of said CD8$^+$ T-cell with a PD-L1/2$^+$ target cell.

* * * * *

SEQUENCE LISTING

```
<160> NUMBER OF SEQ ID NOS: 30

<210> SEQ ID NO 1
<211> LENGTH: 495
<212> TYPE: DNA
<213> ORGANISM: human

<400> SEQUENCE: 1
atgcagattc ctcaggcccc ttggcctgtc gtgtgggctg tgctccagct gggatggcgg      60
cctggctggt ttctggacag ccccgacaga ccctggaacc cccctacatt ttcccctgcc     120
ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggattgcc ggttcagagt gacccagctg     300
cccaacggcc gggacttcca catgtctgtc gtgcgggcca gacggaacga cagcggcaca     360
tatctgtgcg gcgccatcag cctggccccc aaggcccaga tcaaagagag cctgagagcc     420
gagctgagag tgaccgagag aagggccgaa gtgcctaccg cccacectag cccatctcca     480 agacctgccg gccag                                                      495

<210> SEQ ID NO 2
<211> LENGTH: 165
<212> TYPE: PRT
<213> ORGANISM: human

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140
```

```
Thr Glu Arg Arg Ala Glu Val Pro Thr Ala His Pro Ser Pro Ser Pro
145                 150                 155                 160

Arg Pro Ala Gly Gln
            165

<210> SEQ ID NO 3
<211> LENGTH: 129
<212> TYPE: DNA
<213> ORGANISM: human

<400> SEQUENCE: 3
aagcggggca gaaagaagct gctgtacatc ttcaagcagc ccttcatgcg gcccgtgcag      60
accacccagg aagaggacgg ctgctcctgc cggtttcccg aggaagaaga ggggggctgc     120
gagctctaa                                                             129

<210> SEQ ID NO 4
<211> LENGTH: 42
<212> TYPE: PRT
<213> ORGANISM: human

<400> SEQUENCE: 4

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 5
<211> LENGTH: 81
<212> TYPE: DNA
<213> ORGANISM: human

<400> SEQUENCE: 5
attatctcat tcttcctggc cctgacctct accgccctgc tgtttctgct gttctttctg      60
accctgcggt tcagcgtcgt g                                                81

<210> SEQ ID NO 6
<211> LENGTH: 27
<212> TYPE: PRT
<213> ORGANISM: human

<400> SEQUENCE: 6

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 7
<211> LENGTH: 78
<212> TYPE: DNA
<213> ORGANISM: human

<400> SEQUENCE: 7
ttccagacac tggtcgtggg agtcgtgggc ggcctgctgg gatctctggt gctgctcgtg      60
tgggtgctgg ccgtgatc                                                   78
```

```
<210> SEQ ID NO 8
<211> LENGTH: 26
<212> TYPE: PRT
<213> ORGANISM: human

<400> SEQUENCE: 8

Phe Gln Thr Leu Val Val Gly Val Val Gly Gly Leu Leu Gly Ser Leu
1               5                   10                  15

Val Leu Leu Val Trp Val Leu Ala Val Ile
            20                  25

<210> SEQ ID NO 9
<211> LENGTH: 866
<212> TYPE: DNA
<213> ORGANISM: human

<400> SEQUENCE: 9
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc aacacatcg     180 gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcaggcccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccacccag ccctcaccc       480 aggccagccg gccagttcca aaccctggtg gttggtgtcg tgggcggcct gctgggcagc     540
ctggtgctgc tagtctgggt cctggccgtc atctgctccc gggccgcacg agggacaata     600
ggagccaggc gcaccggcca gcccctgaag gaggacccct cagccgtgcc tgtgttctct     660
gtggactatg gggagctgga tttccagtgg cgagagaaga cccggagcc ccccgtgccc      720 tgtgtccctg agcagacgga gtatgccacc attgtctttc ctagcggaat gggcacctca     780
tcccccgccc gcaggggctc agctgacggc cctcggagtg cccagccact gggcctgagg     840
atggacactg ctcttggccc ctctga                                          866

<210> SEQ ID NO 10
<211> LENGTH: 288
<212> TYPE: PRT
<213> ORGANISM: human

<400> SEQUENCE: 10

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 11
<211> LENGTH: 768
<212> TYPE: DNA
<213> ORGANISM: human

<400> SEQUENCE: 11
atgggaaaca gctgttacaa catagtagcc actctgttgc tggtcctcaa ctttgagagg    60
acaagatcat tgcaggatcc ttgtagtaac tgcccagctg gtacattctg tgataataac   120
aggaatcaga tttgcagtcc ctgtcctcca atagtttcct ccagcgcagg tggacaaagg   180
acctgtgaca tatgcaggca gtgtaaaggt gttttcagga ccaggaagga gtgttcctcc   240
accagcaatg cagagtgtga ctgcactcca gggtttcact gcctggggc aggatgcagc   300 atgtgtgaac aggattgtaa acaaggtcaa gaactgacaa aaaaaggttg taaagactgt   360
tgctttggga catttaacga tcagaaacgt ggcatctgtc gaccctggac aaactgttct   420
ttggatggaa agtctgtgct tgtgaatggg acgaaggaga gggacgtggt ctgtggacca   480
tctccagccg acctctctcc gggagcatcc tctgtgaccc cgcctgcccc tgcgagagag   540
ccaggacact ctccgcagat catctccttc tttcttgcgc tgacgtcgac tgcgttgctc   600
ttcctgctgt tcttcctcac gctccgtttc tctgttgtta acggggcag aaagaaactc   660 ctgtatatat tcaaacaacc atttatgaga ccagtacaaa ctactcaaga ggaagatggc   720
tgtagctgcc gatttccaga agaagaagaa ggaggatgtg aactgtga             768

<210> SEQ ID NO 12
<211> LENGTH: 255
<212> TYPE: PRT
<213> ORGANISM: human

<400> SEQUENCE: 12

Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Arg Thr Cys Asp Ile
    50                  55                  60

Cys Arg Gln Cys Lys Gly Val Phe Arg Thr Arg Lys Glu Cys Ser Ser
65              70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 13
<211> LENGTH: 663
<212> TYPE: DNA
<213> ORGANISM: human

<400> SEQUENCE: 13
atgctcaggc tgctcttggc tctcaactta ttcccttcaa ttcaagtaac aggaaacaag    60
attttggtga agcagtcgcc catgcttgta gcgtacgaca atgcggtcaa ccttagctgc   120
aagtattcct acaatctctt ctcaagggag ttccgggcat cccttcacaa aggactggat   180
agtgctgtgg aagtctgtgt tgtatatggg aattactccc agcagcttca ggtttactca   240
aaaacggggt tcaactgtga tgggaaattg gcaatgaatc agtgacattc tacctccag    300 aatttgtatg ttaaccaaac agatatttac ttctgcaaaa ttgaagttat gtatcctcct   360
ccttacctag acaatgagaa agcaatggaa accattatcc atgtgaaagg gaaacacctt   420
tgtccaagtc ccctattttc cggaccttct aagcccttt gggtgctggt ggtggttggt   480
ggagtcctgg cttgctatag cttgctagta acagtggcct tattattttt ctgggtgagg   540
agtaagagga gcaggctcct gcacagtgac tacatgaaca tgactccccg ccgcccggg    600

```
cccacccgca agcattacca gccctatgcc ccaccacgcg acttcgcagc ctatcgctcc    660
tga                                                                  663
```

<210> SEQ ID NO 14
<211> LENGTH: 220
<212> TYPE: PRT
<213> ORGANISM: human

<400> SEQUENCE: 14

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 15
<211> LENGTH: 867
<212> TYPE: DNA
<213> ORGANISM: murine

<400> SEQUENCE: 15

```
atgtgggtcc ggcaggtacc ctggtcattc acttgggctg tgctgcagtt gagctggcaa     60
tcagggtggc ttctagaggt ccccaatggg ccctggaggt ccctcacctt ctacccagcc    120
tggctcacag tgtcagaggg agcaaatgcc accttcacct gcagcttgtc caactggtcg    180
gaggatctta tgctgaactg gaaccgcctg agtcccagca accagactga aaacaggcc     240 gccttctgta tggtttgag ccaacccgtc caggatgccc gcttccagat catacagctg    300
cccaacaggc atgacttcca catgaacatc cttgacacac ggcgcaatga cagtggcatc    360
tacctctgtg gggccatctc cctgcacccc aaggcaaaaa tcgaggagag ccctggagca    420
gagctcgtgg taacagagag aatcctggag acctcaacaa gatatcccag ccctcgccc    480 aaaccagaag gccggtttca aggcatggtc attggtatca tgagtgccct agtgggtatc    540
```

```
cctgtattgc tgctgctggc ctgggcccta gctgtcttct gctcaacaag tatgtcagag    600
gccagaggag ctggaagcaa ggacgacact ctgaaggagg agccttcagc agcacctgtc    660
cctagtgtgg cctatgagga gctggacttc cagggacgag agaagacacc agagctccct    720
accgcctgtg tgcacacaga atatgccacc attgtcttca ctgaagggct gggtgcctcg    780
gccatgggac gtaggggctc agctgatggc ctgcagggtc ctcggcctcc aagacatgag    840
gatggacatt gttcttggcc tctttga                                         867
```

<210> SEQ ID NO 16
<211> LENGTH: 288
<212> TYPE: PRT
<213> ORGANISM: murine

<400> SEQUENCE: 16

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285
```

<210> SEQ ID NO 17
<211> LENGTH: 651
<212> TYPE: DNA
<213> ORGANISM: murine

<400> SEQUENCE: 17

```
atgggaaaca actgttacaa cgtggtggtc attgtgctgc tgctagtggg ctgtgagaag      60
gtgggagccg tgcagaactc ctgtgataac tgtcagcctg gtactttctg cagaaaatac     120
aatccagtct gcaagagctg ccctccaagt accttctcca gcataggtgg acagccgaac     180
tgtaacatct gcagagtgtg tgcaggctat ttcaggttca agaagttttg ctcctctacc     240
cacaacgcgg agtgtgagtg cattgaagga ttccattgct ggggccaca gtgcaccaga      300
tgtgaaaagg actgcaggcc tggccaggag ctaacgaagc agggttgcaa aacctgtagc     360
ttgggaacat ttaatgacca gaacggtact ggcgtctgtc gaccctggac gaactgctct     420
ctagacggaa ggtctgtgct taagaccggg accacggaga aggacgtggg aggaccagga     480
gggcactcct tgcaggtcct taccttgttc ctggcgctga catcggctta attcccccac     540
atattcaagc aaccatttaa gaagaccact ggagcagctc aagaggaaga tgcttgtagc     600
tgccgatgtc cacaggaaga agaaggagga ggaggaggct atgagctgtg a              651
```

<210> SEQ ID NO 18
<211> LENGTH: 256
<212> TYPE: PRT
<213> ORGANISM: murine

<400> SEQUENCE: 18

```
Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Ala Leu Ile Phe Ile Thr Leu Leu Phe
        195                 200                 205

Ser Val Leu Lys Trp Ile Arg Lys Lys Phe Pro His Ile Phe Lys Gln
    210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255
```

<210> SEQ ID NO 19
<211> LENGTH: 657
<212> TYPE: DNA
<213> ORGANISM: murine

<400> SEQUENCE: 19

```
atgacactca ggctgctgtt cttggctctc aacttcttct cagttcaagt aacagaaaac    60
aagattttgg taaagcagtc gcccctgctt gtggtagata gcaacgaggt cagcctcagc   120
tgcaggtatt cctacaacct tctcgcaaag gaattccggg catccctgta caagggcgtg   180
aacagcgacg tggaagtctg tgtcgggaat gggaattta cctatcagcc ccagtttcgc    240
tcgaatgccg agttcaactg cgacggggat ttcgacaacg aaacagtgac gttccgtctc   300
tggaatctgc acgtcaatca cacagatatt tacttctgca aaattgagtt catgtaccct   360
ccgccttacc tagacaacga gaggagcaat ggaactatta ttcacataaa agagaaacat   420
ctttgtcata ctcagtcatc tcctaagctg ttttgggcac tggtcgtggt tgctggagtc   480
ctgttttgtt atggcttgct agtgacagtg gctctttgtg ttatctggac aaatagtaga   540
aggaacagac tccttcaagt gactaccatg aacatgactc cccggaggcc tgggctcact   600
cgaaagcctt accagcccta cgcccctgcc agagactttg cagcgtaccg cccctga      657
```

<210> SEQ ID NO 20
<211> LENGTH: 218
<212> TYPE: PRT
<213> ORGANISM: murine

<400> SEQUENCE: 20

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Val Thr Thr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215
```

<210> SEQ ID NO 21
<211> LENGTH: 705
<212> TYPE: DNA
<213> ORGANISM: human

<400> SEQUENCE: 21

| | | | | | |
|---|---|---|---|---|---|
| atgcagattc | ctcaggcccc | ttggcctgtc | gtgtgggctg | tgctccagct | gggatggcgg | 60 |
| cctggctggt | ttctggacag | ccccgacaga | ccctggaacc | ccctacatt | ttcccctgcc | 120 |
| ctgctggtcg | tgaccgaggg | cgacaatgcc | accttcacct | gtagcttcag | caacaccagc | 180 |
| gagagcttcg | tgctgaactg | gtacagaatg | agccccagca | accagaccga | caagctggcc | 240 |
| gccttccccg | aggatagatc | tcagcccggc | caggactgcc | ggttcagagt | gacccagctg | 300 |
| cccaacggcc | gggacttcca | catgtctgtc | gtgcgggcca | gacggaacga | cagcggcaca | 360 |
| tatctgtgcg | gcgccatcag | cctggccccc | aaggcccaga | tcaaagagag | cctgagagcc | 420 |
| gagctgagag | tgaccgagag | aagggccgaa | gtgcctaccg | ccacccctag | ccatctcca | 480 |
| agacctgccg | gccagattat | tcattcttc | ctggccctga | cctctaccgc | cctgctgttt | 540 |
| ctgctgttct | ttctgacccct | gcggttcagc | gtcgtgaagc | ggggcagaaa | gaagctgctg | 600 |
| tacatcttca | agcagccctt | catgcggccc | gtgcagacca | cccaggaaga | ggacggctgc | 660 |
| tcctgccggt | ttcccgagga | agaagagggg | ggctgcgagc | tctaa | | 705 |

<210> SEQ ID NO 22
<211> LENGTH: 230
<212> TYPE: PRT
<213> ORGANISM: human

<400> SEQUENCE: 22

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ile Ile Phe Phe Leu Ala Leu Thr Ser Thr
                165                 170                 175

Ala Leu Leu Phe Leu Leu Phe Phe Leu Thr Leu Arg Phe Ser Val Val
        180                 185                 190

Lys Arg Gly Arg Lys Lys Leu Leu Tyr Ile Phe Lys Gln Pro Phe Met
    195                 200                 205

```
Arg Pro Val Gln Thr Thr Gln Glu Glu Asp Gly Cys Ser Cys Arg Phe
    210                 215                 220
Pro Glu Glu Glu Glu Gly
225                 230

<210> SEQ ID NO 23
<211> LENGTH: 702
<212> TYPE: DNA
<213> ORGANISM: human

<400> SEQUENCE: 23
atgcagattc ctcaggctcc ttggcctgtc gtgtgggccg tgctccagct gggatggcgg      60
cctggatggt tcctggacag ccccgacaga ccctggaacc cccctacatt ttcccctgcc    120
ctgctggtcg tgaccgaggg cgacaatgcc accttcacct gtagcttcag caacaccagc    180
gagagcttcg tgctgaactg gtacagaatg agccccagca accagaccga caagctggcc    240
gccttccccg aggatagatc tcagcccggc caggactgcc ggttcagagt gacccagctg    300
cccaacggcc gggacttcca catgtctgtc gtgcgcgcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccacccctag cccatctcca    480 agacctgccg gccagttcca gacactggtc gtgggagtcg tgggcggcct gctgggatct    540
ctggtgctgc tcgtgtgggt gctggccgtg atcaagcggg gcagaaagaa gctgctgtac    600
atcttcaagc agcccttcat gcggcccgtg cagaccaccc aggaagagga cggctgctcc    660
tgccggtttc ccgaggaaga agagggggc tgcgagctct aa                         702

<210> SEQ ID NO 24
<211> LENGTH: 233
<212> TYPE: PRT
<213> ORGANISM: human

<400> SEQUENCE: 24

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175
```

```
Leu Leu Gly Ser Leu Val Leu Leu Val Trp Val Leu Ala Val Ile Lys
            180                 185                 190
Arg Gly Arg Lys Lys Leu Leu Tyr Ile Phe Lys Gln Pro Phe Met Arg
        195                 200                 205
Pro Val Gln Thr Thr Gln Glu Glu Asp Gly Cys Ser Cys Arg Phe Pro
    210                 215                 220
Glu Glu Glu Glu Gly Gly Cys Glu Leu
225                 230

<210> SEQ ID NO 25
<211> LENGTH: 702
<212> TYPE: DNA
<213> ORGANISM: human

<400> SEQUENCE: 25
atgcagattc ctcaggcccc ttggcctgtc gtgtgggctg tgctccagct gggatggcgg      60
cctggctggt ttctggacag ccccgacaga ccctggaacc ccctacatt tttcccctgcc    120 ctgctggtcg tgaccgaggg cgacaatgcc accttcacct gtagcttcag caacaccagc    180
gagagcttcg tgctgaactg gtacagaatg agccccagca accagaccga caagctggcc    240
gccttccccg aggatagatc tcagcccggc caggattgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccaccctag cccatctcca    480
agacctgccg ccagttctg gtgctggtg gtcgtgggcg gagtgctggc ctgttacagc    540
ctgctcgtga ccgtggcctt catcatcttt tgggtgcgca gcaagcggag ccggctgctg    600
cacagcgact acatgaacat gacccccaga cggccaggcc ccaccagaaa gcactaccag    660
ccttacgccc ctcccagaga cttcgccgcc tacagaagct ga                       702

<210> SEQ ID NO 26
<211> LENGTH: 233
<212> TYPE: PRT
<213> ORGANISM: human

<400> SEQUENCE: 26

Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
```

```
Thr Glu Arg Arg Ala Glu Val Pro Thr Ala His Pro Ser Pro Ser Pro
145                 150                 155                 160

Arg Pro Ala Gly Gln Phe Trp Val Leu Val Val Gly Gly Val Leu
            165                 170                 175

Ala Cys Tyr Ser Leu Leu Val Thr Val Ala Phe Ile Ile Phe Trp Val
            180                 185                 190

Arg Ser Lys Arg Ser Arg Leu Leu His Ser Asp Tyr Met Asn Met Thr
            195                 200                 205

Pro Arg Arg Pro Gly Pro Thr Arg Lys His Tyr Gln Pro Tyr Ala Pro
            210                 215                 220

Pro Arg Asp Phe Ala Ala Tyr Arg Ser
225                 230
```

<210> SEQ ID NO 27
<211> LENGTH: 483
<212> TYPE: PRT
<213> ORGANISM: human

<400> SEQUENCE: 27

```
Met Gln Ile Pro Gln Ala Pro Trp Pro Val Val Trp Ala Val Leu Gln
1               5                   10                  15

Leu Gly Trp Arg Met Gln Lys Gly Asp Gln Asn Pro Gln Ile Ala Ala
            20                  25                  30

His Val Ile Ser Glu Ala Ser Ser Lys Thr Thr Ser Val Leu Gln Trp
        35                  40                  45

Ala Glu Lys Gly Tyr Tyr Thr Met Ser Asn Asn Leu Val Thr Leu Glu
    50                  55                  60

Asn Gly Lys Gln Leu Thr Val Lys Arg Gln Gly Leu Tyr Tyr Ile Tyr
65                  70                  75                  80

Ala Gln Val Thr Phe Cys Ser Asn Arg Glu Ala Ser Ser Gln Ala Pro
                85                  90                  95

Phe Ile Ala Ser Leu Cys Leu Lys Ser Pro Gly Arg Phe Glu Arg Ile
            100                 105                 110

Leu Leu Arg Ala Ala Asn Thr His Ser Ser Ala Lys Pro Cys Gly Gln
            115                 120                 125

Gln Ser Ile His Leu Gly Gly Val Phe Glu Leu Gln Pro Gly Ala Ser
    130                 135                 140

Val Phe Val Asn Val Thr Asp Pro Ser Gln Val Ser His Gly Thr Gly
145                 150                 155                 160

Phe Thr Ser Phe Gly Leu Leu Lys Leu Gly Gly Gly Ser Gly Gly
            165                 170                 175

Gly Gly Asp Glu Pro Lys Ser Cys Asp Lys Thr His Thr Cys Pro Pro
            180                 185                 190

Cys Pro Ala Pro Pro Val Ala Gly Pro Ser Val Phe Leu Phe Pro Pro
            195                 200                 205

Lys Pro Lys Asp Thr Leu Met Ile Ala Arg Thr Pro Glu Val Thr Cys
            210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
                245                 250                 255

Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
            275                 280                 285
```

-continued

```
Lys Ala Leu Pro Ala Pro Ile Glu Lys Thr Ile Ser Lys Ala Lys Gly
            290                 295                 300

Gln Pro Arg Glu Pro Gln Val Tyr Thr Leu Pro Pro Ser Arg Asp Glu
305                 310                 315                 320

Leu Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
        355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys Gly Pro Ser Lys Pro Phe
                405                 410                 415

Trp Val Leu Val Val Val Gly Gly Val Leu Ala Cys Tyr Ser Leu Leu
            420                 425                 430

Val Thr Val Ala Phe Ile Ile Phe Trp Val Arg Ser Lys Arg Ser Arg
        435                 440                 445

Leu Leu His Ser Asp Tyr Met Asn Met Thr Pro Arg Arg Pro Gly Pro
450                 455                 460

Thr Arg Lys His Tyr Gln Pro Tyr Ala Pro Pro Arg Asp Phe Ala Ala
465                 470                 475                 480

Tyr Arg Ser

<210> SEQ ID NO 28
<211> LENGTH: 348
<212> TYPE: PRT
<213> ORGANISM: human

<400> SEQUENCE: 28

Met Gln Ile Pro Gln Ala Pro Trp Pro Val Val Trp Ala Val Leu Gln
1               5                   10                  15

Leu Gly Trp Arg Met Gln Lys Gly Asp Gln Asn Pro Gln Ile Ala Ala
            20                  25                  30

His Val Ile Ser Glu Ala Ser Ser Lys Thr Thr Ser Val Leu Gln Trp
        35                  40                  45

Ala Glu Lys Gly Tyr Tyr Thr Met Ser Asn Asn Leu Val Thr Leu Glu
    50                  55                  60

Asn Gly Lys Gln Leu Thr Val Lys Arg Gln Gly Leu Tyr Tyr Ile Tyr
65                  70                  75                  80

Ala Gln Val Thr Phe Cys Ser Asn Arg Glu Ala Ser Ser Gln Ala Pro
                85                  90                  95

Phe Ile Ala Ser Leu Cys Leu Lys Ser Pro Gly Arg Phe Glu Arg Ile
            100                 105                 110

Leu Leu Arg Ala Ala Asn Thr His Ser Ser Ala Lys Pro Cys Gly Gln
        115                 120                 125

Gln Ser Ile His Leu Gly Gly Val Phe Glu Leu Gln Pro Gly Ala Ser
    130                 135                 140

Val Phe Val Asn Val Thr Asp Pro Ser Gln Val Ser His Gly Thr Gly
145                 150                 155                 160

Phe Thr Ser Phe Gly Leu Leu Lys Leu Gly Gly Gly Ser Gly Gly
                165                 170                 175
```

```
Gly Gly Asp Gly Gln Ala Cys Asn Pro Ser Ala Cys Arg Ala Val Gly
            180                 185                 190

Arg Gly Leu Gln Pro Lys Gly Val Arg Val Lys Glu Thr Ala Asp Phe
        195                 200                 205

Lys Val Tyr Thr Lys Gly Ala Gly Ser Gly Glu Leu Lys Val Thr Val
    210                 215                 220

Lys Gly Pro Lys Gly Glu Glu Arg Val Lys Gln Lys Asp Leu Gly Asp
225                 230                 235                 240

Gly Val Tyr Gly Phe Glu Tyr Tyr Pro Met Val Pro Gly Thr Tyr Ile
                245                 250                 255

Val Thr Ile Thr Trp Gly Gly Gln Asn Ile Gly Arg Ser Pro Phe Glu
            260                 265                 270

Val Lys Val Gly Pro Ser Lys Pro Phe Trp Val Leu Val Val Val Gly
        275                 280                 285

Gly Val Leu Ala Cys Tyr Ser Leu Leu Val Thr Val Ala Phe Ile Ile
    290                 295                 300

Phe Trp Val Arg Ser Lys Arg Ser Arg Leu Leu His Ser Asp Tyr Met
305                 310                 315                 320

Asn Met Thr Pro Arg Arg Pro Gly Pro Thr Arg Lys His Tyr Gln Pro
                325                 330                 335

Tyr Ala Pro Pro Arg Asp Phe Ala Ala Tyr Arg Ser
                340                 345

<210> SEQ ID NO 29
<211> LENGTH: 290
<212> TYPE: PRT
<213> ORGANISM: human

<400> SEQUENCE: 29

Met Arg Ser Lys Arg Ser Arg Leu Leu His Ser Asp Tyr Met Asn Met
1               5                   10                  15

Thr Pro Arg Arg Pro Gly Pro Thr Arg Lys His Tyr Gln Pro Tyr Ala
            20                  25                  30

Pro Pro Arg Asp Phe Ala Ala Tyr Arg Ser Ala Thr Gly Leu Pro Ile
        35                  40                  45

Ser Met Lys Ile Phe Met Tyr Leu Leu Thr Val Phe Leu Ile Thr Gln
    50                  55                  60

Met Ile Gly Ser Ala Leu Phe Ala Val Tyr Leu His Arg Arg Leu Asp
65                  70                  75                  80

Lys Ile Glu Asp Glu Arg Asn Leu His Glu Asp Phe Val Phe Met Lys
                85                  90                  95

Thr Ile Gln Arg Cys Asn Thr Gly Glu Arg Ser Leu Ser Leu Leu Asn
            100                 105                 110

Cys Glu Glu Ile Lys Ser Gln Phe Glu Gly Phe Val Lys Asp Ile Met
        115                 120                 125

Leu Asn Lys Glu Glu Thr Lys Lys Glu Asn Ser Phe Glu Met Gln Lys
    130                 135                 140

Gly Asp Gln Asn Pro Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                165                 170                 175

Met Ser Asn Asn Leu Val Thr Leu Glu Asn Gly Lys Gln Leu Thr Val
            180                 185                 190

Lys Arg Gln Gly Leu Tyr Tyr Ile Tyr Ala Gln Val Thr Phe Cys Ser
        195                 200                 205
```

```
Asn Arg Glu Ala Ser Ser Gln Ala Pro Phe Ile Ala Ser Leu Cys Leu
    210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                245                 250                 255

Val Phe Glu Leu Gln Pro Gly Ala Ser Val Phe Val Asn Val Thr Asp
                260                 265                 270

Pro Ser Gln Val Ser His Gly Thr Gly Phe Thr Ser Phe Gly Leu Leu
                275                 280                 285

Lys Leu
    290

<210> SEQ ID NO 30
<211> LENGTH: 261
<212> TYPE: PRT
<213> ORGANISM: human

<400> SEQUENCE: 30

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```